(12) United States Patent
Umaña et al.

(10) Patent No.: US 8,021,856 B2
(45) Date of Patent: Sep. 20, 2011

(54) ANTIBODY GLYCOSYLATION VARIANTS HAVING INCREASED ANTIBODY-DEPENDENT CELLULAR CYTOTOXICITY

(75) Inventors: Pablo Umaña, Zurich (CH); Joël Jean-Mairet, Barcelona (CH); James E. Bailey, Santa Monica, CA (US); M. Sean Bailey, legal representative, Santa Monica, CA (US)

(73) Assignee: Roche GlycArt AG, Zürich (CH)

( * ) Notice: Subject to any disclaimer, the term of this patent is extended or adjusted under 35 U.S.C. 154(b) by 589 days.

(21) Appl. No.: 11/199,232

(22) Filed: Aug. 9, 2005

(65) Prior Publication Data

US 2005/0272128 A1 Dec. 8, 2005
US 2008/0280322 A9 Nov. 13, 2008

Related U.S. Application Data

(60) Continuation of application No. 10/211,554, filed on Aug. 5, 2002, now abandoned, application No. 11/199,232, filed on Aug. 9, 2005, which is a continuation-in-part of application No. 10/633,697, filed on Aug. 5, 2003, now Pat. No. 7,517,670, which is a division of application No. 09/294,584, filed on Apr. 20, 1999, now Pat. No. 6,602,684.

(60) Provisional application No. 60/309,516, filed on Aug. 3, 2001, provisional application No. 60/082,581, filed on Apr. 20, 1998.

(51) Int. Cl.
*C12P 21/08* (2006.01)
*A61K 39/395* (2006.01)
(52) U.S. Cl. .............. 435/69.1; 424/130.1; 435/70.21
(58) Field of Classification Search .................. None
See application file for complete search history.

(56) References Cited

U.S. PATENT DOCUMENTS

| | | | |
|---|---|---|---|
| 4,215,051 A | 7/1980 | Schroeder et al. |
| 4,946,778 A | 8/1990 | Ladner et al. |
| 4,978,745 A | 12/1990 | Schoemaker et al. |
| 5,047,335 A | 9/1991 | Paulson et al. |
| 5,529,922 A | 6/1996 | Chapman et al. |
| 5,547,933 A | 8/1996 | Lin |
| 5,736,137 A | 4/1998 | Anderson et al. |
| 5,753,229 A | 5/1998 | Mordoh et al. |
| 5,776,456 A | 7/1998 | Anderson et al. |
| 5,843,439 A | 12/1998 | Anderson et al. |
| 5,939,068 A | 8/1999 | Brams et al. |
| 5,952,203 A | 9/1999 | Withers et al. |
| 5,958,403 A | 9/1999 | Strom et al. |
| 6,153,433 A | 11/2000 | Miyoshi et al. |
| 6,183,744 B1 | 2/2001 | Goldenberg |
| 6,602,684 B1 | 8/2003 | Umaña et al. |
| 2003/0175884 A1 | 9/2003 | Umaña et al. |
| 2004/0072290 A1 | 4/2004 | Umaña et al. |
| 2005/0074843 A1 | 4/2005 | Umaña et al. |

FOREIGN PATENT DOCUMENTS

| | | |
|---|---|---|
| AU | 2002307037 B2 | 10/2002 |
| CN | 1555411 A | 12/2004 |
| EP | 0 475 354 A2 | 3/1992 |
| EP | 0 669 836 B1 | 7/1996 |
| EP | 0 752 248 A1 | 1/1997 |
| JP | 2005-524379 A | 8/2005 |
| WO | WO 94/11026 | 5/1994 |
| WO | WO 95/24494 | 9/1995 |
| WO | WO 97/30087 | 8/1997 |
| WO | WO 97/30087 A1 | 8/1997 |
| WO | WO 98/06835 A2 | 2/1998 |
| WO | WO 99/54342 A1 | 10/1999 |
| WO | WO 00/67795 | 11/2000 |
| WO | WO 02/079255 A1 | 10/2002 |
| WO | WO 03/011878 A2 | 2/2003 |

OTHER PUBLICATIONS

ATCC page entry for YB2/0 cells, printed Jan. 31, 2010, 2 pages.*
Amstutz, H., et al., "Production and Characterization of a Mouse/Human Chimeric Antibody Directed Against Human Neuroblastoma," *Int. J. Cancer* 53:147-152, Wiley-Liss, Inc. (1993).
Anderson, W.F., "Human gene therapy," *Nature* 392:25-30, Nature Pub. Co. (1998).
Arathoon, W.R., and Birch, J.R., "Large-Scale Cell Culture in Biotechnology," *Science* 232:1390-1395, American Association for the Advancement of Science (1986).
Bailey, J.E., "Toward a Science of Metabolic Engineering," *Science* 252:1668-1675, American Association for the Advancement of Science (1991).
Bailey, J.E., et al., "Engineering Glycosylation in Animal Cells," in *New Developments and New Applications in Animal Cell Technology*, Merten, O.W., et. al., eds., Kluwer Academic Publishers, The Netherlands, pp. 5-23 (1998).
Bailey, J.E., et al., "Metabolic Engineering of N-Linked Glycoform Synthesis Systems in Chinese Hamster Ovary (CHO) Cells," in *Animal Cell Technology*, Carrondo, M.J.T., et. al., eds., Kluwer Academic Publishers, The Netherlands, pp. 489-494 (1997).
Bibila, T.A., and Flickinger, M.C., "A Model of Interorganelle Monoclonal Antibody Transport and Secretion in Mouse Hybridoma Cells," *Biotechnol. Bioeng.* 38:767-780, John Wiley & Sons, Inc. (1991).
Bibila, T.A., and Robinson, D.K., "In Pursuit of the Optimal Fed-Batch Process for Monoclonal Antibody Production," *Biotechnol. Prog.* 11:1-13, American Chemical Society and American Institute of Chemical Engineers (1995).
Bitter, G.A., "Heterologous Gene Expression in Yeast," *Meth. Enzymol.* 152:673-684, Academic Press, Inc. (1987).
Bitter, G.A., et al., "Expression and Secretion Vectors for Yeast," *Meth. Enzymol.* 153:516-544, Academic Press, Inc. (1987).

(Continued)

*Primary Examiner* — Michael Burkhart
(74) *Attorney, Agent, or Firm* — Sterne, Kessler, Goldstein & Fox P.L.L.C.

(57) ABSTRACT

The present invention relates to the field of glycosylation engineering of proteins. More particularly, the present invention relates to glycosylation engineering to generate proteins with improved therapeutic properties, including antibodies with increased antibody-dependent cellular cytotoxicity.

19 Claims, 11 Drawing Sheets

OTHER PUBLICATIONS

Boyd, P.N., et al., "The Effect of the Removal of Sialic Acid, Galactose and Total Carbohydrate on the Functional Activity of Campath-1H," *Molec. Immunol.* 32:1311-1318, Pergamon Press (1995).

Bretscher, M.S., and Munro, S., "Cholesterol and the Golgi Apparatus," *Science* 261:1280-1281, American Association for the Advancement of Science (1993).

Briles, E.B., et al., "Isolation of Wheat Germ Agglutinin-resistant Clones of Chinese Hamster Ovary Cells Deficient in Membrane Sialic Acid and Galactose," *J. Biol. Chem.* 252:1107-1116, American Society for Biochemistry and Molecular Biology, Inc. (1977).

Brisson, N., et al., "Expression of a bacterial gene in plants by using a viral vector," *Nature* 310:511-514, Nature Pub. Co. (1984).

Brockhausen, I., et al., "Control of glycoprotein synthesis. Characterization of (1 4)-$N$-acetyl-$\beta$-D-glucosaminyltransferases acting on the $\alpha$-D-(1 3)-and $\alpha$-D-(1 6)-linked arms of $N$-linked oligosaccharides," *Carbohydrate Res.* 236:281-299, Elsevier Science Publishers B.V. (1992).

Broglie, R., et al., "Light-Regulated Expression of a Pea Ribulose-1,5-Biphosphate Carboxylase Small Subunit Gene in Transformed Plant Cells," *Science* 224:838-843, American Association for the Advancement of Science (1984).

Campbell, C., and Stanley, P., "A Dominant Mutation to Ricin Resistance in Chinese Hamster Ovary Cells Induces UDP-GlcNAc:Glycopeptide $\beta$-4-$N$-Acetylglucosaminyltransferase III Activity," *J. Biol. Chem.* 261:13370-13378, American Society for Biochemistry and Molecular Biology, Inc. (1984).

Caruthers, M.H., et al., "New chemical methods for synthesizing polynucleotides," *Nuc. Acids Res. Symp. Series* 7:215-223, IRL Press Limited (1980).

Chow, F., et al., "Synthesis of oligodeoxyribonucleotides on silica del support," *Nuc. Acids Res.* 9:2807-2817, IRL Press Limited (1981).

Cole, N.B., et al., "Diffusional Mobility of Golgi Proteins in Membranes of Living Cells," *Science* 273:797-801, American Association for the Advancement of Science (1996).

Cole, S.P.C., et al., "The EBV-Hybridoma Technique and its Application to Human Lung Cancer," in *Monoclonal Antibodies and Cancer Therapy*, Reisfeld, R.A., and Sell, S., eds., Alan R. Liss, Inc., New York, NY, pp. 77-96 (1985).

Coruzzi, G., et al., "Tissue-specific and light-regulated expression of a pea nuclear gene encoding the small subunit of ribulose-1,5-biphosphate carboxylase," *EMBO J.* 3:1671-1679, IRL Press Limited (1984).

Cote, R.J., et al., "Generation of human monoclonal antibodies reactive with cellular antigens," *Proc. Natl. Acad. Sci.* 80:2026-2030, The National Academy of Sciences (1983).

Crea, R., and Horn, T., "Synthesis of oligonucleotides on cellulose by a phosphotriester method," *Nuc. Acids Res.* 8:2331-2348, IRL Press Limited (1980).

Creighton, T.E., *Proteins: Structures and Molecular Principles*, W.H. Freeman and Co., New York, NY, pp. 34-60 (1983).

Cumming, D.A., "Glycosylation of recombinant protein therapeutics: control and functional implications," *Glycobiology* 1:115-130, Oxford University Press (1991).

Davies, J. et al., "Expression of GnTIII in a Recombinant Anti-CD20 Production Cell Line: Expression of Antibodies with Altered Glycoforms Leads to an Increase in ADCC Through Higher Affinity for Fc$\gamma$RIII," *Biotechnol. Bioeng.* 74:288-294, John Wiley & Sons, Inc. (Aug. 2001).

De Bree, R., et al., "Clinical screening of monoclonal antibodies 323/A3, cSF-25 and K928 for suitability of targetting tumours in the upper aerodigestive and respiratory tract," *Nucl. Med. Commun.* 15:613-627, Lippincott, Williams & Wilkins (1994).

Dennis, J.W., et al., "$\beta$1-6 Branching of Asn-Linked Oligosaccharides Is Directly Associated with Metastasis," *Science* 236:582-585, American Association for the Advancement of Science (1987).

Do, K.-Y., "Modification of Glycoproteins by $N$-Acetylglucosaminyltransferase V Is Greatly Influenced by Accessibility of the Enzyme to Oligosaccharide Acceptors," *J. Biol. Chem.* 269:23456-23464, American Society for Biochemistry and Molecular Biology (1994).

Dörr, U., et al., "First Clinical Results with the Chimeric Antibody chCE7 in Neuroblastoma. Targeting Features and Biodistribution Data," *Eur. J. Nucl. Med.* 20:858, Springer International (1993).

Dunphy, W.G., and Rothman, J.E., "Compartmentation of Asparagine-linked Oligosaccharide Processing in the Golgi Apparatus," *J. Cell. Bio.* 97:270-275, Rockefeller University Press (1983).

Dunphy, W.G., et al., "Attachment of Terminal N-Acetylglucosamine to Asparagine-Linked Oligosaccharide Occurs in Central Cisternae of the Golgi Stack," *Cell* 40:463-472, MIT (1985).

Dunphy, W.G., et al., "Early and late functions associated with the Golgi apparatus reside in distinct compartments," *Proc. Natl. Acad. Sci.* 78:7453-7457, The National Academy of Sciences (1981).

Dürrbach, A., et al., "Antibody-mediated endocytosis of G250 tumor-associated antigen allows targeted gene transfer to human renal cell carcinoma in vitro," *Cancer Gene Ther.* 6:564-571, Nature Publishing Group (Nov.-Dec. 1999).

Dwek, R.A., "Glycobiology: More Functions for Oligosaccharides," *Science* 269:1234-1235, American Association for the Advancement of Science (1995).

Easton, E.W., et al., "Enzymatic Amplification Involving Glycosyltransferases Forms the Basis for the Increased Size of Asparagine-linked Glycans at the Surface of NIH 3T3 Cells Expressing the N-*ras* Proto-oncogene," *J. Biol. Chem.* 266:21674-21680, American Society for Biochemistry and Molecular Biology (1991).

Edge, C.J., et al., "The conformational effects of N-linked glycosylation," *Biochem. Soc. Trans.* 21:452-455, Portland Press (1993).

Elices, M.J., and Goldstein, I.J., "Ehrlich Ascites Tumor Cell UDP-Gal:$N$-Acetyl-D-glucosamine $\beta$(1,4)-Galactosyltransferase," *J. Biol. Chem.* 263:3354-3362, American Society for Biochemistry and Molecular Biology, Inc. (1988).

Elion, E.A., "Enzymatic Manipulation of DNA and RNA," in *Current Protocols in Molecular Biology*, Ausubel, F., et al., eds., John Wiley and Sons, New York, NY, pp. 3.17.1-3.17.10 (1998).

English language abstract of European Patent Publication No. 481 790 A, Derwent WPI Accession No. 1992-134048 (1992).

English language abstract of European Patent Publication No. 585 083 A1, Derwent WPI Accession No. 1994-067563 (1994).

English language abstract of German Patent No. De 19546680 A1, Derwent WPI Accession No. 1997-321072 (Jun. 1997).

English language abstract of International Patent Publication No. WO 00/52135 A2, Derwent WPI Accession No. 2000-572178 (Sep. 2000).

English language abstract of International Patent Publication No. WO 00/53730 A2, Derwent WPI Accession No. 2000-594316 (Sep. 2000).

English language abstract of International Patent Publication No. WO 01/29242 A2, Derwent WPI Accession No. 2001-290925 (Apr. 2001).

English language abstract of International Patent Publication No. WO 94/12646 A1, Derwent WPI Accession No. 1994-200274 (1994).

English language abstract of International Patent Publication No. WO 95/15769 A1, Derwent WPI Accession No. 1995-224151 (1995).

English language abstract of International Patent Publication No. WO 97/34632 A1, Derwent WPI Accession No. 1997-479995 (Sep. 1997).

English language abstract of International Patent Publication No. WO 98/49198 A1, Derwent WPI Accession No. 1998-080758 [07] (Nov. 1998).

English language abstract of International Patent Publication No. WO 96/13516 A1, Derwent WPI Accession No. 1996-239446 (1996).

English language abstract of International Patent Publication No. WO 98/58964 A1, Derwent WPI Accession No. 1999-081223 (Dec. 1998).

English language abstract of Japanese Patent No. JP 09084582 A, Derwent WPI Accession No. 1997-253000 (Mar. 1997).

English language abstract of United States Patent No. 5,714,350 A, Derwent WPI Accession No. 1998-129858 (Feb. 1998).

Fanger, M.W., et. al., "Cytotoxicity mediated by human Fc receptors for IgG," *Immunol. Today* 10:92-99, Elsevier Science Publishers (1989).

Field, M., et. al., "The Use of High-Performance Anion-Exchange Chromatography and Matrix-Assisted Laser Desorption/Ionization Time-of-Flight Mass Spectrometry to Monitor and Identify Oligosaccharide Degradation," *Anal. Biochem.* 239:92-98, Academic Press, Inc. (1996).

Fouser, L.A., et. al., "High Level Expression of a Chimeric Anti-Ganglioside GD2 Antibody: Genomic Kappa Sequences Improve Expression in COS and CHO Cells," *Biotechnology* 10:1121-1127, Nature Pub. Co. (1992).

Frost, J.D., et. al., "A Phase I/IB Trial of Murine Monoclonal Anti-GD2 Antibody 14.G2a plus Interleukin-2 in Children with Refractory Neuroblastoma," *Cancer* 80:317-333, American Cancer Society (1997).

Fukuta, K., et al., "Control of Bisecting GlcNAc Addition to N-Linked Sugar Chains," *J. Biol. Chem.* 275:23456-23461, The American Society for Biochemistry and Molecular Biology, Inc. (Aug. 2000).

Goldberg, D.E., and Kornfeld, S., "Evidence for Extensive Subcellular Organization of Asparagine-linked Oligosaccharide Processing and Lysosomal Enzyme Phosphorylation," *J. Biol. Chem.* 258:3159-3165, American Society for Biochemistry and Molecular Biology, Inc. (1983).

Goochee, C.F., et al., "The Oligosaccharides of Glycoproteins: Factors Affecting their Synthesis and their Influence on Glycoprotein Properties," in *Frontiers in Bioprocessing II*, Todd, P., et. al., eds., American Chemical Society, Washington, DC, pp. 199-240 (1992).

Gossen, M., et al., "Control of gene activity in higher eukaryotic cells by prokaryotic regulatory elements," *TIBTECH* 12:58-62, Elsevier Science Ltd. (1994).

Graham, R.A., et al., "The polymorphic epithelial mucin: potential as an immunogen for a cancer vaccine," *Cancer Immunol. Immunother.* 42:71-80, Springer-Verlag (1996).

Grierson, D., and Covey, S.N., *Plant Molecular Biology, 2nd edition*, Blackie Publishing, London, GB, Chapters 7-9 (1988).

Griffiths, G., et al., "The Dynamic Nature of the Golgi Complex," *J. Cell Bio.* 108:277-297, Rockefeller University Press (1989).

Gross, H.J., et al., "A Highly Sensitive Fluorometric Assay for Sialyltransferase Activity Using CMP-9-fluoresceinyl-NeuAc as Donor," *Analyt. Biochem.* 186:127-134, Academic Press, Inc. (1990).

Gu, J., et al., "Purification and Characterization of UDP-N-Acetylglucosamine: α-6-D-Mannoside β1-6N-Acetylglucosaminyltransferase (N-Acetylglucosaminyltransferase V) from a Human Lung Cancer Cell Line," *J. Biochem.* 113:614-619, Tokyo Japanese Biochemical Society (1993).

Gurley, W.B., et al., "Upstream Sequences Required for Efficient Expression of a Soybean Heat Shock Gene," *Mol. Cell. Bio.* 6:559-565, American Society for Microbiology (1986).

Haga, Y., et al., "Dose-Related Comparison of Antibody-Dependent Cellular Cytotoxicity with Chimeric and Native Murine Monoclonal Antibody 17-1A," *Int. J. Pancreatol.* 15:43-50, Humana Press Inc. (1994).

Harpaz, N., and Schachter, H., "Control of Glycoprotein Synthesis," *J. Biol. Chem.* 255:4894-4902, American Society for Biochemistry and Molecular Biology, Inc. (1980).

Harvey, D.J., "Quantitative Aspects of the Matrix-assisted Laser Desorption Mass Spectrometry of Complex Oligosaccharides," *Rapid Commun. Mass Spectrom.* 7:614-619, John Wiley & Sons, Ltd. (1993).

Hirschberg, C.B., and Snider, M.D., "Topography of Glycosylation in the Rough Endoplasmic Reticulum and Golgi Apparatus," *Ann. Rev. Biochem.* 56:63-87, Annual Reviews Inc. (1987).

Huse, W.D., et al., "Generation of a Large Combinatorial Library of the Immunoglobin Repertoire in Phage Lambda," *Science* 246:1275-1281, American Association for the Advancement of Science (1989).

Jefferis, R. and Lund, J., "Glycosylation of Antibody Molecules: Structural and Functional Significance," *Chem. Immunol.* 65:111-128, Karger (Jan. 1997).

Jefferis, R., et al., "Effector mechanisms activated by human IgG subclass antibodies: clinical and molecular aspects," *Ann. Biol. Clin..* 52:57-65, John Libbey Eurotext (1994).

Jefferis, R., et al., "IgG-Fc-mediated effector functions: molecular definition of interaction sites for effector ligands and the role of glycosylation," *Immunol. Rev.* 163:59-76, Munksgaard (Jun. 1998).

Jefferis, R., et al., "Recognition sites on human IgG for Fcγ receptors: the role of glycosylation," *Immunology Letters* 44:111-117, Elsevier Science B.V. (1995).

Jenkins, N., and Curling, E.M.A., "Glycosylation of recombinant proteins: Problems and prospects," *Enzyme Microb. Technol.* 16:354-364, Butterworth-Heinemann (1994).

Jenkins, N., et al., "Getting the glycosylation right: Implications for the biotechnology industry," *Nat. Biotechnol.* 14:975-981, Nature Pub. Co. (1996).

Kagawa, Y., et al., "Comparative Study of the Asparagine-linked Sugar Chains of Natural Human Interferon-β1 and Recombinant Human Interferon-β1 Produced by Three Different Mammalian Cells," *J. Biol. Chem.* 263:17508-17515, American Society for Biochemistry and Molecular Biology, Inc. (1988).

Kaszubowski, P.A., et al., "A Cytotoxic Monoclonal Antibody to Colon Adenocarcinoma," *Cancer Res.* 44:1194-1197, American Association for Cancer Research (1984).

Kilmartin, J.V., et al., "Rat Monoclonal Antitubulin Antibodies Derived by Using a New Nonsecreting Rat Cell Line," *J. Cell Biol.* 93:576-582, The Rockefeller University Press (1982).

Koenig, A., "Selectin inhibition: synthesis and evaluation of novel sialylated, sulfated and fucosylated oligosaccharides, including the major capping group of GlyCAM-1," *Glycolobiology* 7:79-93, Oxford University Press (1997).

Küster, B., et al., "Sequencing of N-Linked Oligosaccharides Directly from Protein Gels: In-Gel Deglycosylation Followed by Matrix-Assisted Laser Desorption/Ionization Mass Spectrometry and Normal-Phase High-Performance Liquid Chromatography," *Analyt. Biochem.* 250:82-101, Academic Press (1997).

Köhler, G., and Milstein, C., "Continuous cultures of fused cells secreting antibody of predefined specificity," *Nature* 256:495-497, Nature Pub. Co. (1975).

Kolber, M.A., et al., "Measurement of cytotoxicity by target cell release and retention of the fluorescent dye bis-carboxyethyl-carboxyfluorescein (BCECF)," *J. Immunol. Meth.* 108:255-264, Elsevier Science Publishers B.V. (1988).

Kornfeld, R., and Kornfeld, S., "Assembly of Asparagine-Linked Oligosaccharides," *Ann. Rev. Biochem.* 54:631-664, Annual Reviews Inc. (1985).

Kozbor, D., and Roder, J.C., "The production of monoclonal antibodies from human lymphocytes," *Immunol. Today* 4:72-79, Elsevier Biomedical Press (1983).

Lifely, M.R., et al., "Glycosylation and biological activity of CAMPATH-1H expressed in different cell lines and grown under different culture conditions," *Glycobiology* 5:813-822, Oxford University Press (1995).

Lis, H., and Sharon, N., "Protein glycosylation: Structural and functional aspects," *Eur. J. Biochem.* 218:1-27, FEBS (1993).

Lloyd, K.O., et al., "Comparison of O-Linked Carbohydrate Chains in MUC-1 Mucin from Normal Breast Epithelial Cell Lines and Breast Carcinoma Cell Lines," *J. Biol. Chem.* 271:33325-33334, American Society for Biochemistry and Molecular Biology, Inc. (1996).

Luiten, R.M., et al., "Chimeric immunoglobulin E reactive with tumor-associated antigen activates human FcεRI bearing cells," *Hum. Antibodies* 8:169-180, IOS Press (Dec. 1997).

Lund, J., "Multiple Interactions of IgG with Its Core Oligosaccharide Can Modulate Recognition by Complement and Human Fcγ Receptor I and Influence the Synthesis of Its Oligosaccharide Chains," *J. Immunol.* 157:4963-4969, The American Association of Immunologists (1996).

Lund, J., et al., "Control of IgG/Fc Glycosylation: A Comparison of Oligosaccharides from Chimeric Human/Mouse and Mouse Subclass Immunoglobulin Gs," *Mol. Immunol.* 30:741-748, Pergamon Press Ltd. (1993).

Lund, J., et. al., "Oligosaccharide-protein interactions in IgG can modulate recognition by Fcγ receptors," *Res. Commun.* 9:115-119, FASEB (1995).

Malhotra, R., et al., "Glycosylation changes of IgG associated with rheumatoid arthritis can activate complement via the mannose-binding protein," *Nat. Med.* 1:237-243, Nature Pub. Co. (1995).

Marshall, E., "Gene therapy's growing pains," *Science* 269:1050-1055, American Association for the Advancement of Science (1995).

Matteucci, M.D., and Caruthers, M.H., "The Synthesis of Oligodeoxypyrimidines on a Polymer Support," *Tetrahedron Lett.* 21:719-722, Pergamon Press Ltd. (1980).

Misaizu, T., et al., "Role of Antennary Structure of N-Linked Sugar Chains in Renal Handling of Recombinant Human Erythropoietin," *Blood* 86:4097-4104, The American Society of Hematology (1995).

Moremen, K.W., et al., "Glycosidases of the asparagine-linked oligosaccharide processing pathway," *Glycobiology* 4:113-125, Oxford University Press (1994).

Morgan, A., et al., "The N-terminal end of the $C_H2$ domain of chimeric human IgG1 anti-HLA-DR is necessary for C1q, FcγRI and FcγRIII binding," *Immunology* 86:319-324, Blackwell Science Ltd. (1995).

Morrison, S.L., et al., "Chimeric human antibody molecules: Mouse antigen-binding domains with human constant region domains," *Proc. Natl. Acad. Sci. USA* 81:6851-6855, National Academy of Sciences (1984).

Murakami, H., et al., "Human-Human Hybridomas Secreting Antibodies Specific to Human Lung Carcinoma," *In Vitro Cell. Develop. Biol.* 21:593-596, Tissue Culture Association, Inc. (1985).

Nakamura, K., et al., "Chimeric Anti-Ganglioside $G_{M2}$ Antibody with Antitumor Activity," *Cancer Research* 54:1511-1516, American Association for Cancer Research (1994).

Narasimhan, S., "Control of Glycoprotein Synthesis," *J. Biol. Chem.* 257:10235-10242, American Society for Biochemistry and Molecular Biology, Inc. (1982).

Narasimhan, S., et al., "Control of Glycoprotein Synthesis. Bovine Milk UDPgalactose: N-Acetylglucosamine β-4-Galactosyltransferase Catalyzes the Preferential Transfer of Galactose to the GlcNAcβ1,2Manα1,3-Branch of both Bisected and Nonbisected Complex Biantennary Asparagine-Linked Oligosaccharides," *Biochemistry* 24:1694-1700, American Chemical Society (1985).

Naven, T.J.P., and Harvey, D.J., "Effect of Structure on the Signal Strength of Oligosaccharides in Matrix-assisted Laser Desorption/Ionization Mass Spectrometry on Time-of-flight and Magnetic Sector Instruments," *Rapid Commun. Mass Spectrom.* 10:1361-1366, John Wiley & Sons, Ltd. (1996).

Neuberger, M.S., et al., "Recombinant antibodies possessing novel effector functions," *Nature* 312:604-608, Nature Pub. Co. (1984).

Nilsson, T., et al., "Kin recognition between *medial* Golgi enzymes in HeLa cells," *EMBO J.* 13:562-574, Oxford University Press (1994).

Nilsson, T., et al., "Overlapping Distribution of Two Glycotransferases in the Golgi Apparatus of HeLa Cells," *J. Cell Biol.* 120:5-13, Rockefeller University Press (1993).

Nilsson, T., et al., "The role of the membrane-spanning domain and stalk region of N-acetylglucosaminyltransferase I in retention, kin recognition and structural maintenance of the Golgi apparatus in HeLa cells," *J. Cell Sci.* 109:1975-1989, The Company of Biologists Limited (1996).

Nishikawa, A., et al., "Purification, cDNA Cloning, and Expression of UDP-N-acetylglucosamine:β-D-mannoside β-1,4N-Acetylglucosaminyltransferase III from Rat Kidney," *J. Biol. Chem.* 267:18199-18204, American Society for Biochemistry and Molecular Biology, Inc. (1992).

Ohno, M., et al., "Enzymatic Basis of Sugar Structures of α-Fetoprotein in Hepatoma and Hepatoblastoma Cell Lines: Correlation with Activities of α1-6 Fucosyltransferase and N-Acetylglucosaminyltransferases III and V," *Int. J. Cancer* 51:315-317, Wiley-Liss, Inc. (1992).

Orkin, S.H, and Motulsky, A.G., "Report and recommendations of the panel to assess the NIH investment in research on gene therapy," Dec. 7, 1995, available at <http://www.nih.gov/news/panelrep.html>.

Page, M.J., and Sydenham, M.A., "High Level Expression of the Humanized Monoclonal Antibody CAMPATH-1H in Chinese Hamster Ovary Cells," *Biotechnology* 9:64-68, Nature Pub. Co. (1991).

Palcic, M.M., et al., "Regulation of N-Acetylglucosaminyltransferase V Activity," *J. Biol. Chem.* 265:6759-6769, American Society for Biochemistry and Molecular Biology, Inc. (1990).

Pâquet, M.R., et al., "Branch Specificity of Purified Rat Liver Golgi UDP-galactose:N-Acetylglucosamine β-1,4-Galactosyltransferase," *J. Biol. Chem.* 259:4716-4721, American Society for Biochemistry and Molecular Biology, Inc. (1984).

Paulson, J.C., and Colley, K.J., "Glycosyltransferases," *J. Biol. Chem.* 264:17615-17618, American Society for Biochemistry and Molecular Biology, Inc. (1989).

Pels Rijcken, W.R., et al., "The effect of increasing nucleotide-sugar concentrations on the incorporation of sugars into glycoconjugates in rat hepatocytes," *Biochem. J.* 305:865-870, UK Biochemical Society (1995).

Rabouille, C., et al., "Mapping the distribution of Golgi enzymes involved in the construction of complex oligosaccharides," *J. Cell Sci.* 108:1617-1627, The Company of Biologists Limited (1995).

Raju, T.S., et al., "Species-specific variation in glycosylation of IgG: evidence for the species-specific sialylation and branch-specific galactosylation and importance for engineering recombinant glycoprotein therapeutics," *Glycobiology* 10:477-486, IRL Press at Oxford University Press (2000).

Rao, A.K., and Mendicino, J., "Influence of Glycopeptide Structure on the Regulation of Galactosyltransferase Activity," *Biochemistry* 17:5632-5638, American Chemical Society (1978).

Rearick, J.I., et al., "Enzymatic Characterization of β-D-Galactoside α2 3 Sialyltransferase from Porcine Submaxillary Gland," *J. Biol. Chem.* 254:4444-4451, American Society for Biochemistry and Molecular Biology, Inc. (1979).

Reff, M.E., et al., "Depletion of B Cells In Vivo by a Chimeric Mouse Human Monoclonal Antibody to CD20," *Blood* 83:435-445, American Society of Hematology (1994).

Riechmann, L., et al., "Reshaping human antibodies for therapy," *Nature* 332:323-327, Nature Pub. Co. (1988).

Robinson, R.R., et al., "Chimeric mouse-human anti-carcinoma antibodies that mediate different anti-tumor cell biological activities," *Hum. Antibod. Hybridomas* 2:84-93, Butterworth-Heinemann (1991).

Rogers, S.G., et al., "Gene Transfer in Plants: Production of Transformed Plants Using Ti Plasmid Vectors," in *Methods for Plant Molecular Biology,* Weissbach, A., and Weissbach, H., eds., Academic Press, Inc., San Diego, CA, pp. 423-463 (1988).

Roman, H., "Development of Yeast as an Experimental Organism," in *The Molecular Biology of the Yeast Saccharomyces, Life Cycle and Inheritance,* Strathern, J.N., et al., eds., Cold Spring Harbor Laboratory Press, Cold Spring Harbor, NY, pp. 1-9 (1981).

Rothman, J.E., and Orci, L., "Molecular dissection of the secretory pathway," *Nature* 355:409-415, Nature Pub. Co. (1992).

Rothman, J.E., and Wieland, F.T., "Protein Sorting by Transport Vesicles," *Science* 272:227-234, American Association for the Advancement of Science (1996).

Rothman, R.J., et al., "Antibody-Dependent Cytotoxicity Mediated by Natural Killer Cells Is Enhanced by Castanospermine-Induced Alterations of IgG Glycosylation," *Mol. Immunol.* 26:1113-1123, Pergamon Press (1989).

Rothman, R.J., et al., "Clonal Analysis of the Glycosylation of Immunoglobulin G Secreted by Murine Hybridomas," *Biochemistry* 28: 1377-1384, American Chemical Society (1989).

Rothstein, R., "Cloning in Yeast," in *DNA Cloning Column II: a practical approach,* Glover, D.M., ed., IRL Press, Washington, DC, pp. 45-66 (1985).

Routier, F.H., et al., "The glycosylation pattern of a humanized IgG1 antibody (D1.3) expressed in CHO cells," *Glycoconjugate J.* 14:201-207, Chapman & Hall (Feb. 1997).

Russo, R.N., et al., "β1,4-Galactosyltransferase: A Short $NH_2$-terminal Fragment That Includes the Cytoplasmic and Transmembrane Domain Is Sufficient for Golgi Retention," *J. Biol. Chem.* 267:9241-9247, American Society for Biochemistry and Molecular Biology, Inc. (1992).

Sambanis, A., et al., "A Model of Secretory Protein Trafficking in Recombinant AtT-20 Cells," *Biotech. And Biotechnol. Bioeng.* 38:280-295, John Wiley & Sons, Inc. (1991).

Sambrook, J., et al., *Molecular Cloning, A Laboratory Manual, 2nd Edition,* Cold Spring Harbor Laboratory Press, Cold Spring Harbor, NY, pp. 8.1-9.62 (1989).

Sburlati, A., et al., "Novel glycoform of recombinant human IFN-β by overexpression of N-acetyl glucosaminyltransferase II," *Glycoconj. J.* 14:781, Kluwer Academic Publishing (1997).

Sburlati, A.R., et al., "Synthesis of Bisected Glycoforms of Recombinant IFN-β by Overexpression of β-1,4-N-Acetylglucosaminyltransferase III in Chinese Hamster Ovary Cells," *Biotechnol. Prog.* 14:189-192, American Chemical Society (Mar.-Apr. 1998).

Schachter, H., "Biosynthetic controls that determine the branching and microheterogenicity of protein-bound oligosaccharides," *Biochem. Cell. Biol.* 64:163-181, National Research Council of Canada (1986).

Shao, M.-C., and Wold, F., "The Effect of the Protein Matrix on Glycan Processing in Glycoproteins," *J. Biol. Chem.* 263:5771-5774, American Society for Biochemistry and Molecular Biology, Inc., 1989.

Shao, M-C., and Wold, F., "The effect of the protein matrix proximity on glycan reactivity in a glycoprotein model," *Eur. J. Biochem.* 228:79-85, FEBS (1995).

Sheares, B.T., Robbins, P.W., "Glycosylation of ovalbumin in a heterologous cell: Analysis of oligosaccharide chains of the cloned glycoprotein in mouse L cells," *Proc. Natl. Acad. Sci.* 83:1993-1997, National Academy of Sciences (1986).

Shelikoff, M., et al., "A Modeling Framework for the Study of Protein Glycosylation," *Biotechnol. Bioeng.* 50:73-90, John Wiley & Sons, Inc. (1996).

Sheng, Y., et al., "Remodeling of Glycoconjugates on CD44 Enhances Cell Adhesion to Hyaluronate, Tumor Growth and Metastasis in B16 Melanoma Cells Expressing β1, 4-N-Acetylglucosaminyltransferase III," *Int. J. Cancer* 73:850-858, Wiley-Liss, Inc. (Dec. 1997).

Shields, R.L., et al., "Lack of Fucose on Human IgG1 N-Linked Oligosaccharide Improves Binding to Human FcγRIII and Antibody-dependent Cellular Toxicity," *J. Biol. Chem.* 277:26733-26740, The American Society for Biochemistry and Molecular Biology, Inc. (electronically available May 2002).

Shinkawa, T., et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.* 278:3466-3473, American Society for Biochemistry and Molecular Biology (2003).

Shitara, K., et al., "A new vector for the high level expression of chimeric antibodies in myeloma cells," *J. Immunol. Methods* 167:271-278, Elsevier Science (1991).

Smith, G.E., et al., "Molecular Engineering of the *Autographa californica* Nuclear Polyhedrosis Virus Genome: Deletion Mutations Within the Polyhedrin Gene," *J. Virol.* 46:584-593, American Society for Microbiology (1983).

Spellman, M.W., et al., "Carbohydrate Structures of Human Tissue Plasminogen Activator Expressed in Chinese Hamster Ovary Cells," *J. Biol. Chem.* 264:14100-14111, American Society for Biochemistry and Molecular Biology, Inc. (1989).

Standley, P., et al., "CHO cells provide access to novel N-gylcans and developmentally regulated glycosyltransferases," *Glycobiology* 6:695-699, Oxford University Press (1996).

Standley, S. and Baudry, M., "The role of glycosylation in ionotropic glutamate receptor ligand binding, function, and trafficking," *Cell. Mol. Life Sci.* 57:1508-1516, Birkhäuser Verlag (Oct. 2000).

Struhl, K., "Subcloning of DNA Fragments," in *Current Protocols in Molecular Biology,* Ausubel, F., et al., eds., John Wiley and Sons, New York, NY, pp. 3.16.1-3.16.11 (1998).

Surfus, J.E., et al., "Anti-Renal-Cell Carcinoma Chimeric Antibody G250 Facilitates Antibody-Dependent Cellular Cytotoxicity with in Vitro and in Vivo Interleukin-2-Activated Effectors," *J. Immunother.* 19:184-191, Raven Press (1996).

Tabas, I., and Kornfeld, S., "Purification and Characterization of a Rat Liver Golgi α-Mannosidase Capable of Processing Asparagine-linked Oligosaccharides," *J. Biol. Chem.* 254:11655-11663, American Society for Biochemistry and Molecular Biology, Inc. (1979).

Takamatsu, N., et al., "Expression of bacterial chloramphenicol acetyltransferase gene in tobacco plants mediated by TMV-RNA," *EMBO J.* 6:307-311, IRL Press Limited (1987).

Takeda, S-i. et al., "Construction of chimaeric processed immunoglobulin genes containing mouse variable and human constant region sequences," *Nature* 314:452-454, Nature Pub. Co. (1985).

Tanemura, M., et al., "Reduction of the Major Swine Xenoantigen GALα(1,3)GAL by Transfection of N-Acetylglucosaminyl Transferase III (GnT-III) Gene," *Transplantation Proc.* 29:891-892, Elsevier Science Inc. (1997).

Taniguchi, N., et al., "Glycosyltransferase Assays Using Pyridylaminated Acceptors: N-Acetylglucosaminyltransferase III, IV, and V," *Meth. Enzymol.* 179:397-408, Academic Press, Inc. (1989).

Trill, J.J., et al., "Production of monoclonal antibodies in COS and CHO cells," *Curr. Opin. Biotechnol.* 6:553-560, Current Biology Ltd. (1995).

Umaña, P., et al., "Tetracycline-Regulated Overexpression of Glycosyltransferases in Chinese Hamster Ovary Cells," *Biotechnol. Bioeng.* 65:542-549, John Wiley & Sons, Inc. (Dec. 1999).

Umaña, P., et al., "Engineered glycoforms of an antineuroblastoma IgG1 with optimized antibody-dependent cellular cytotoxic activity," *Nat. Biotechnol.* 17:176-180, Nature Pub. Co. (1999).

Valone, F.H., et al., "Phase Ia/Ib Trial of Bispecific Antibody MDX-210 in Patients with Advanced Breast or Ovarian Cancer That Overexpresses the Proto-Oncogene HER-2/*neu*," *J. Clin. Oncol.* 13:2281-2292, American Society for Clinical Oncology (1995).

Velasco, A., et al., "Cell Type-dependent Variations in the Subcellular Distribution of α-Mannosidase I and II," *J. Cell. Biol.* 122:39-51, Rockefeller University Press (1993).

Varki, A., "Biological roles of oligosaccharides: all of the theories are correct," *Glycobiology* 3:97-130, Oxford University Press (1993).

Verma, I.M., et al., "Gene therapy—promises, problems and prospects," *Nature* 389:239-242, Nature Pub. Co. (1997).

Watson, E., et al., "Structure determination of the intact major sialylated oligosaccharide chains of recombinant human erythropoietin expressed in Chinese hamster ovary cells," *Glycobiology* 4:227-237, Oxford University Press (1994).

Wiest, D.L., et al., "Membrane Biogenesis during B Cell Differentiation: Most Endoplasmic Reticulum Proteins are Expressed Coordinately," *J. Cell. Biol.* 110:1501-1511, Rockefeller University Press (1990).

Wright, A., and Morrison, S.L., "Effect of glycosylation on antibody function: implications for genetic engineering," *Trends Biotechnol.* 15:26-32, Elsevier Science Publishers (Jan. 1997).

Wright, A., and Morrison, S.L., "Effect of Altered $C_H2$-associated Carbohydrate Structure on the Functional Properties and in Vivo Fate of Chimeric Mouse-Human Immunoglobulin G1," *J. Exp. Med.* 180:1087-1096, The Rockefeller University Press (Sep. 1994).

Wyss, D.F., and Wagner, G., "The structural role of sugars in glycoproteins," *Curr. Opin. Biotechnol.* 7:409-416, Current Biology Ltd. (1996).

Yamaguchi, N., and Fukuda, M.N., "Golgi Retention Mechanism of β-1,4-Galactosyltransferase," *J. Biol. Chem.* 270:12170-12176, American Society for Biochemistry and Molecular Biology, Inc. (1995).

Yoshimura, M., et al., "Suppression of lung metastasis of B16 mouse melanoma by N-acetylglucosaminyltransferase III gene transfection," *Proc. Natl. Acad. Sci. USA* 92:8754-8758, National Academy of Sciences (1995).

Youakim, A. and Shur, B.D., "Alteration of Oligosaccharide Biosynthesis by Genetic Manipulation of Glycosyltransferases," *Ann. N.Y. Acad. Sci.* 745:331-335, New York Academy of Sciences (1994).

Yu Ip, C.C., et al., "Structural Characterization of the N-Glycans of a Humanized Anti-CD18 Murine Immunoglobulin G," *Arch. Biochem. Biophys.* 308:387-399, Academic Press, Inc. (1994).

International Search Report for International Application No. PCT/US99/08711, European Office, Netherlands, mailed on Aug. 17, 1999.

Search Report of Subject Search Conducted by Swiss Federal Institute of Intellectual Property Concerning WO 99/54342 (published international application corresponding to U.S. Appl. No. 08/294,548) dated Jul. 18, 2001.

Supplementary European Search Report for European Application No. 99 91 8731, mailed Dec. 17, 2004, European Patent Office, The Hague.

Office Action for U.S. Appl. No. 10/437,388, Umaña et al., filed May 14, 2003, mailed on Oct. 26, 2006.

Office Action for U.S. Appl. No. 10/437,388, Umaña et al., filed May 14, 2003, mailed on Jul. 25, 2007.

Office Action for U.S. Appl. No. 10/633,699, Umaña et al., filed Aug. 5, 2003, mailed on Apr. 12, 2005.

Office Action for U.S. Appl. No. 10/633,699, Umaña et al., filed Aug. 5, 2003, mailed on Mar. 23, 2006.

Office Action for U.S. Appl. No. 10/633,699, Umaña et al., filed Aug. 5, 2003, mailed on Oct. 31, 2003.

Office Action for U.S. Appl. No. 10/633,697, Umaña et al., filed Aug. 5, 2003, mailed on Apr. 11, 2006.

Office Action for U.S. Appl. No. 10/633,697, Umaña et al., filed Aug. 5, 2003, mailed on Sep. 10, 2007.

Office Action for U.S. Appl. No. 10/211,554, Umaña et al., filed Aug. 5, 2002, mailed on Feb. 9, 2005.

International Search Report for International Application No. PCT/US02/24739, United States Patent and Trademark Office, Alexandria, VA, mailed on Jul. 23, 2003.

Supplementary European Search Report for European Patent Application No. 02778191.3, mailed Apr. 15, 2005, European Patent Office, The Hague.

International Preliminary Examination Report for International Application No. PCT/US2002/024739, completed Jul. 12, 2005.

Dialog File 351, Accession No. 13156779, English language abstract for CN 155541 A and JP 2005-524379 (listed as document FP12 and FP13 respectively on accompanying PTO/SB/08A), 2007.

Office Action for U.S. Appl. No. 10/437,388, Umaña et al., filed May 14, 2003, mailed on Jan. 24, 2008.

Office Action for U.S. Appl. No. 10/633,697, Umaña et al., filed Aug. 5, 2003, mailed on Jan. 10, 2008.

Office Action for U.S. Appl. No. 10/633,699, Umaña et al., filed Aug. 5, 2003, mailed on Nov. 15, 2007.

Buske, C., et al., "Monoclonal Antibody Therapy for B Cell Non-Hodgkin's Lymphomas: Emerging Concepts of a Tumour-targeted Strategy," *European Journal of Cancer* 35:549-557, Elsevier Science Ltd. (1999).

Maloney, D.G., at al., "Phase I Clinical Trial Using Escalating Single-Dose Infusion of Chimeric Anti-CD20 Monoclonal Antibody (IDEC-C2B8) in Patients With Recurrent B-Cell Lymphoma," *Blood* 84:2457-2466, The American Society of Hematology (1994).

Novak-Hofer, I., et al., "Cellular Processing of Copper-67-labeled Monoclonal Antibody chCE7 by Human Neuroblastoma Cells," *Cancer Research* 55:46-50, The American Association for Cancer Research (1995).

Anderson, et al., "Targeted anti-cancer therapy using rituximab, a chimeric anti-CD20 antibody (IDEC-C2B8) in the treatment of non-Hodgkin's B-cell lymphoma," *Biochemical Society Transactions*, 25(2):705-708, The Biochemical Society, United States (May 1997).

Ratanatharathorn, V., et al., "Anti-CD20 Chimeric Monoclonal Antibody Treatment of Refractory Immune-Mediated Thrombocytopenia in a Patient with Chronic Graft-versus-Host Disease" *Annals of Internal Medicine*, 133(4):275-279, American College of Physicians, United States (2000).

Zecca, M., et al., Anti-CD20 monoclonal antibody for the treatment of severe, immune-mediated, pure red cell aplasia and hemolytic anemia *Blood*, 97(12):3995-3997, The American Society of Hematology, United States (2001).

Office Action mailed Oct. 1, 2008 in U.S. Appl. No. 10/633,697, Umana et al., filed Aug. 5, 2003.

Office Action mailed Dec. 10, 2008, in U.S. Appl. No. 10/437,388, Umaña et al., filed May 14, 2003.

Office Action mailed Feb. 3, 2009, in U.S. Appl. No. 10/633,699, Umaña et al., filed Aug. 5, 2003.

Office Action mailed Nov. 25, 2009, in U.S. Appl. No. 10/633,699, Umaña et al., filed Aug. 5, 2003.

* cited by examiner

ANTIBODY GLYCOSYLATION VARIANTS HAVING INCREASED ANTIBODY-DEPENDENT CELLULAR CYTOTOXICITY

CROSS-REFERENCE TO RELATED APPLICATIONS

This application is a continuation of U.S. application Ser. No. 10/211,554, filed Aug. 5, 2002, now abandoned, which claims the benefit of Appl. No. 60/309,516, filed Aug. 3, 2001 and a continuation-in-part of U.S. application Ser. No. 10/633,697, filed Aug. 5, 2003 (pending), which is a divisional of application Ser. No. 09/294,584, now issued U.S. Pat. No. 6,602,684, which claims the benefit of U.S. Provisional Appl. No. 60/082,581, filed Apr. 20, 1998.

BACKGROUND OF THE INVENTION

1. Field of the Invention

The present invention relates to the field of glycosylation engineering of proteins. More particularly, the present invention relates to glycosylation engineering to generate proteins with improved therapeutic properties, including antibodies with increased antibody-dependent cellular cytotoxicity.

2. Background Art

Glycoproteins mediate many essential functions in human beings, other eukaryotic organisms, and some prokaryotes, including catalysis, signaling, cell-cell communication, and molecular recognition and association. They make up the majority of non-cytosolic proteins in eukaryotic organisms. (Lis et al., *Eur. J. Biochem.* 218:1-27 (1993)). Many glycoproteins have been exploited for therapeutic purposes, and during the last two decades, recombinant versions of naturally-occurring, secreted glycoproteins have been a major product of the biotechnology industry. Examples include erythropoietin (EPO), therapeutic monoclonal antibodies (therapeutic mAbs), tissue plasminogen activator (tPA), interferon-$\beta$, (IFN-$\beta$), granulocyte-macrophage colony stimulating factor (GM-CSF), and human chorionic gonadotrophin (hCG). (Cumming et al., *Glycobiology* 1:115-130 (1991)).

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins et al., *Nature Biotechnol.* 14:975-81 (1996)).

Mammalian cells are the preferred hosts for production of therapeutic glycoproteins, due to their capability to glycosylate proteins in the most compatible form for human application. (Cumming et al., *Glycobiology* 1: 115-30 (1991); Jenkins et al., *Nature Biotechnol.* 14:975-81 (1996)). Bacteria very rarely glycosylate proteins, and like other types of common hosts, such as yeasts, filamentous fungi, insect and plant cells, yield glycosylation patterns associated with rapid clearance from the bloodstream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NS0- and SP2/0-mouse myeloma cells. More recently, production from transgenic animals has also been tested (Jenkins et al., *Nature Biotechnol.* 14:975-81 (1996)).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Morrison, S. L., *Trends Biotech.* 15:26-32 (1997)). The structure of the attached N-linked carbohydrate varies considerably, depending on the degree of processing, and can include high-mannose, multiply-branched as well as biantennary complex oligosaccharides. (Wright, A., and Morrison, S. L., *Trends Biotech.* 15:26-32 (1997)). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R. et al., *Glycobiology* 5(8):813-22 (1995)).

Unconjugated monoclonal antibodies (mAbs) can be useful medicines for the treatment of cancer, as demonstrated by the U.S. Food and Drug Administration's approval of Rituximab (Rituxan™; IDEC Pharmaceuticals, San Diego, Calif., and Genentech Inc., San Francisco, Calif.), for the treatment of CD20 positive B-cell, low-grade or follicular Non-Hodgkin's lymphoma, and Trastuzumab (Herceptin™; Genentech Inc,) for the treatment of advanced breast cancer (Grillo-Lopez, A.-J., et al., *Semin. Oncol.* 26:66-73 (1999); Goldenberg, M. M., *Clin. Ther.* 21:309-18 (1999)). The success of these products relies not only on their efficacy but also on their outstanding safety profiles (Grillo-Lopez, A.-J., et al., *Semin. Oncol.* 26:66-73 (1999); Goldenberg, M. M., *Clin. Ther.* 21:309-18 (1999)). In spite of the achievements of these two drugs, there is currently a large interest in obtaining higher specific antibody activity than what is typically afforded by unconjugated mAb therapy.

One way to obtain large increases in potency, while maintaining a simple production process and potentially avoiding significant, undesirable side effects, is to enhance the natural, cell-mediated effector functions of mAbs by engineering their oligosaccharide component (Umaña, P. et al., *Nature Biotechnol.* 17:176-180 (1999)). IgG1 type antibodies, the most commonly used antibodies in cancer immunotherapy, are glycoproteins that have a conserved N-linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., *Glycobiology* 5:813-822 (1995); Jefferis, R., et al., *Immunol Rev.* 163:59-76 (1998); Wright, A. and Morrison, S. L., *Trends Biotechnol.* 15:26-32 (1997)).

The present inventors showed previously that overexpression in Chinese hamster ovary (CHO) cells of $\beta(1,4)$-N-acetylglucosaminyltransferase III (GnTIII), a glycosyltransferase catalyzing the formation of bisected oligosaccharides, significantly increases the in vitro ADCC activity of an anti-neuroblastoma chimeric monoclonal antibody (chCE7) produced by the engineered CHO cells. (See Umaña, P. et al., *Nature Biotechnol.* 17:176-180 (1999), International Publication No. WO 99/54342, the entire contents of each of which are hereby incorporated by reference in their entirety). The antibody chCE7 belongs to a large class of unconjugated mAbs which have high tumor affinity and specificity, but have too little potency to be clinically useful when produced in standard industrial cell lines lacking the GnTIII enzyme (Umana, P., et al., *Nature Biotechnol.* 17:176-180 (1999)). That study was the first to show that large increases of maximal in vitro ADCC activity could be obtained by increasing the proportion of constant region (Fc)-associated, bisected oligosaccharides above the levels found in naturally occurring antibodies. To determine if this finding could be extrapolated to an unconjugated mAb, which already has significant ADCC activity in the absence of bisected oligosaccharides, the present inventors have applied this technology to Rituximab, the anti-CD20, IDEC-C2B8 chimeric antibody. The present inventors have likewise applied the technology to the unconjugated anti-cancer mAb chG250.

BRIEF SUMMARY OF THE INVENTION

The present inventors have now generated new glycosylation variants of the anti-CD20 monoclonal antibody (mAb) IDEC-C2B8 (Rituximab) and the anti-cancer mAb chG250 using genetically engineered mAb-producing cell lines that overexpress N-acetylglucosaminyltransferase III (GnTIII; EC 2.1.4.144) in a tetracycline regulated fashion. GnTIII is required for the synthesis of bisected oligosaccharides, which are found at low to intermediate levels in naturally-occurring human antibodies but are missing in mAbs produced in standard industrial cell lines. The new glycosylated versions outperformed Mabthera™ (the version of Rixtuximab marketed in Europe) and mouse-myeloma derived chG250 in biological (ADCC) activity. For example, a ten-fold lower amount of the variant carrying the highest levels of bisected oligosaccharides was required to reach the maximal ADCC activity as Mabthera™. For chG250, the variant carrying the highest levels of bisected oligosaccharides mediated significant ADCC activity at a 125-fold lower concentration than that required to detect even low ADCC activity by the unmodified control chG250. A clear correlation was found between the level of GnTIII expression and ADCC activity.

Accordingly, in one aspect the claimed invention is directed to a host cell engineered to produce a polypeptide having increased Fc-mediated cellular cytotoxicity by expression of at least one nucleic acid encoding β(1,4)-N-acetylglucosaminyltransferase III (GnT III), wherein the polypeptide produced by the host cell is selected from the group consisting of a whole antibody molecule, an antibody fragment, and a fusion protein which includes a region equivalent to the Fc region of an immunoglobulin, and wherein the GnT III is expressed in an amount sufficient to increase the proportion of said polypeptide carrying bisected hybrid oligosaccharides or galactosylated complex oligosaccharides or mixtures thereof in the Fc region relative to polypeptides carrying bisected complex oligosaccharides in the Fc region.

In a preferred embodiment, the polypeptide is IgG or a fragment thereof, most preferably, IgG1 or a fragment thereof. In a further preferred embodiment, the polypeptide is a fusion protein that includes a region equivalent to the Fc region of a human IgG.

In another aspect of the claimed invention, a nucleic acid molecule comprising at least one gene encoding GnTIII has been introduced into the host cell. In a preferred embodiment, at least one gene encoding GnTIII has been introduced into the host cell chromosome.

Alternatively, the host cell has been engineered such that an endogenous GnT III gene is activated, for example, by insertion of a DNA element which increases gene expression into the host chromosome. In a preferred embodiment, the endogenous GnTIII has been activated by insertion of a promoter, an enhancer, a transcription factor binding site, a transposon, or a retroviral element or combinations thereof into the host cell chromosome. In another aspect, the host cell has been selected to carry a mutation triggering expression of an endogenous GnTIII. Preferably, the host cell is the CHO cell mutant lec 10.

In a further preferred embodiment of the claimed invention, the at least one nucleic acid encoding a GnTIII is operably linked to a constitutive promoter element.

In a further preferred embodiment, the host cell is a CHO cell, a BHK cell, a NS0 cell, a SP2/0 cell, or a hybridoma cell, a Y0 myeloma cell, a P3X63 mouse myeloma cell, a PER cell or a PER.C6 cell and said polypeptide is an anti-CD20 antibody. In another preferred embodiment, the host cell is a SP2/0 cell and the polypeptide is the monoclonal antibody chG250.

In another aspect, the claimed invention is directed to a host cell that further comprises at least one transfected nucleic acid encoding an antibody molecule, an antibody fragment, or a fusion protein that includes a region equivalent to the Fc region of an immunoglobulin. In a preferred embodiment, the host cell comprises at least one transfected nucleic acid encoding an anti-CD20 antibody, the chimeric anti-human neuroblastoma monoclonal antibody chCE7, the chimeric anti-human renal cell carcinoma monoclonal antibody chG250, the chimeric anti-human colon, lung, and breast carcinoma monoclonal antibody ING-1, the humanized anti-human 17-1A antigen monoclonal antibody 3622W94, the humanized anti-human colorectal tumor antibody A33, the anti-human melanoma antibody directed against GD3 ganglioside R24, or the chimeric anti-human squamous-cell carcinoma monoclonal antibody SF-25, an anti-human EGFR antibody, an anti-human EGFRvIII antibody, an anti-human PSMA antibody, and anti-human PSCA antibody, an anti-human CD22 antibody, an anti-human CD30 antibody, an anti-human CD33 antibody, an anti-human CD38 antibody, an anti-human CD40 antibody, an anti-human CD45 antibody, an anti-human CD52 antibody, an anti-human CD138 antibody, an anti-human HLA-DR variant antibody, an anti-human EpCAM antibody, an anti-human CEA antibody, an anti-human MUC1 antibody, an anti-human MUC1 core protein antibody, an anti-human aberrantly glycosylated MUC1 antibody, an antibody against human fibronectin variants containing the ED-B domain, and an anti-human HER2/neu antibody.

In another aspect, the claimed invention is directed to a method for producing a polypeptide in a host cell comprising culturing any of the above-described the host cells under conditions which permit the production of said polypeptide having increased Fc-mediated cellular cytotoxicity. In a preferred embodiment, the method further comprises isolating said polypeptide having increased Fc-mediated cellular cytotoxicity.

In a further preferred embodiment, the host cell comprises at least one nucleic acid encoding a fusion protein comprising a region equivalent to a glycosylated Fc region of an immunoglobulin.

In a preferred embodiment, the proportion of bisected oligosaccharides in the Fc region of said polypeptides is greater than 50%, more preferably, greater than 70%. In another embodiment, the proportion of bisected hybrid oligosaccharides or galactosylated complex oligosaccharides or mixtures thereof in the Fc region is greater than the proportion of bisected complex oligosaccharides in the Fc region of said polypeptide.

In a preferred aspect of the claimed method, the polypeptide is an anti-CD20 antibody and the anti-CD20 antibodies produced by said host cell have a glycosylation profile, as analyzed by MALDI/TOF-MS, that is substantially equivalent to that shown in FIG. 2E.

In another preferred aspect of the claimed method, the polypeptide is the chG250 monoclonal antibody and the chG250 antibodies produced by said host cell have a glycosylaton profile, as analyzed by MALDI/TOF-MS, that is substantially equivalent to that shown in FIG. 7D.

In a further aspect, the claimed invention is directed to an antibody having increased antibody dependent cellular cytotoxicity (ADCC) produced by any of the methods described above. In preferred embodiments, the antibody is selected from the group consisting of an anti-CD20 antibody, chCE7, ch-G250, a humanized anti-HER2 monoclonal antibody, ING-1, 3622W94, SP-25, A33, and R24. Alternatively, the polypeptide can be an antibody fragment that includes a region equivalent to the Fc region of an immunoglobulin, having increased Fc-mediated cellular cytotoxicity produced by any of the methods described above.

In a further aspect, the claimed invention is directed to a fusion protein that includes a region equivalent to the Fc region of an immunoglobulin and having increased Fc-mediated cellular cytotoxicity produced by any of the methods described above.

In a further aspect, the claimed invention is directed to a pharmaceutical composition comprising the antibody, antibody fragment, or fusion protein of the invention and a pharmaceutically acceptable carrier.

In a further aspect, the claimed invention is directed to a method for the treatment of cancer comprising administering a therapeutically effective amount of said pharmaceutical composition to a patient in need thereof.

In a further aspect, the invention is directed to an improved method for treating an autoimmune disease produced in whole or in part by pathogenic autoantibodies based on B-cell depletion comprising administering a therapeutically effective amount of immunologically active antibody to a human subject in need thereof, the improvement comprising administering a therapeutically effective amount of an antibody having increased ADCC prepared as described above. In a preferred embodiment, the antibody is an anti-CD20 antibody. Examples of autoimmune diseases or disorders include, but are not limited to, immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, post-streptococcal nephritis, erythema nodosum, Takayasu's arteritis, Addison's disease, erythema multiforme, polyarteritis nodosa, ankylosing spondylitis, Goodpasture's syndrome, thromboangitis ubiterans, primary biliary cirrhosis, Hashimoto's thyroiditis, thyrotoxicosis, chronic active hepatitis, polymyositis/dermatomyositis, polychondritis, pamphigus vulgaris, Wegener's granulomatosis, membranous-nephropathy, amyotrophic lateral sclerosis, tabes dorsalis, polymyaglia, pernicious anemia, rapidly progressive glomerulonephritis and fibrosing alveolitis, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type 1 diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious amenia (Addison's disease); diseases involving leukocyte diapedesis; central nervous system (CNS) inflammatory disorder, multiple organ injury syndrome; hemolytic anemia (including, but not limited to cryoglobinemia or Coombs positive anemia); myastheniagravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc. In this aspect of the invention, the antibodies of the invention are used to deplete the blood of normal B-cells for an extended period.

BRIEF DESCRIPTION OF THE FIGURES

(FIG. 3A) The core of the oligosaccharide is composed of three mannose (M) and two N-acetylglucosamine (Gn) monosaccharide residues attached to $Asn_{297}$. Galactose (G), fucose (F), and bisecting N-acetylglucosamine (Gn, boxed) can be present or absent. Terminal N-acetylneuraminic acid may be also present but it is not included in the figure. (FIG. 3B) Partial N-linked glycosylation pathway leading to the formation of the major oligosaccharide classes (dotted frames). Bisecting N-acetylglucosamine is denoted as $Gn^b$. Subscript numbers indicate how many monosaccharide residues are present in each oligosaccharide. Each structure appears together with its sodium-associated [M+Na$^+$] mass. The mass of those structures that contain fucose (f) are also included.

(FIG. 4A) Activity of C2B8 samples derived from a single cell line but produced at increasing GnTIII expression levels (i.e., decreasing tetracycline concentrations). The samples are C2B8-2000t, C2B8-50t, C2B8-25t, and C2B8-nt (control mAb derived from a clone that does not express GnTIII (FIG. 4B) ADCC activity of C2B8-50t and C2B8-25t compared to Mabthera™.

DETAILED DESCRIPTION OF THE INVENTION

Figure 1:
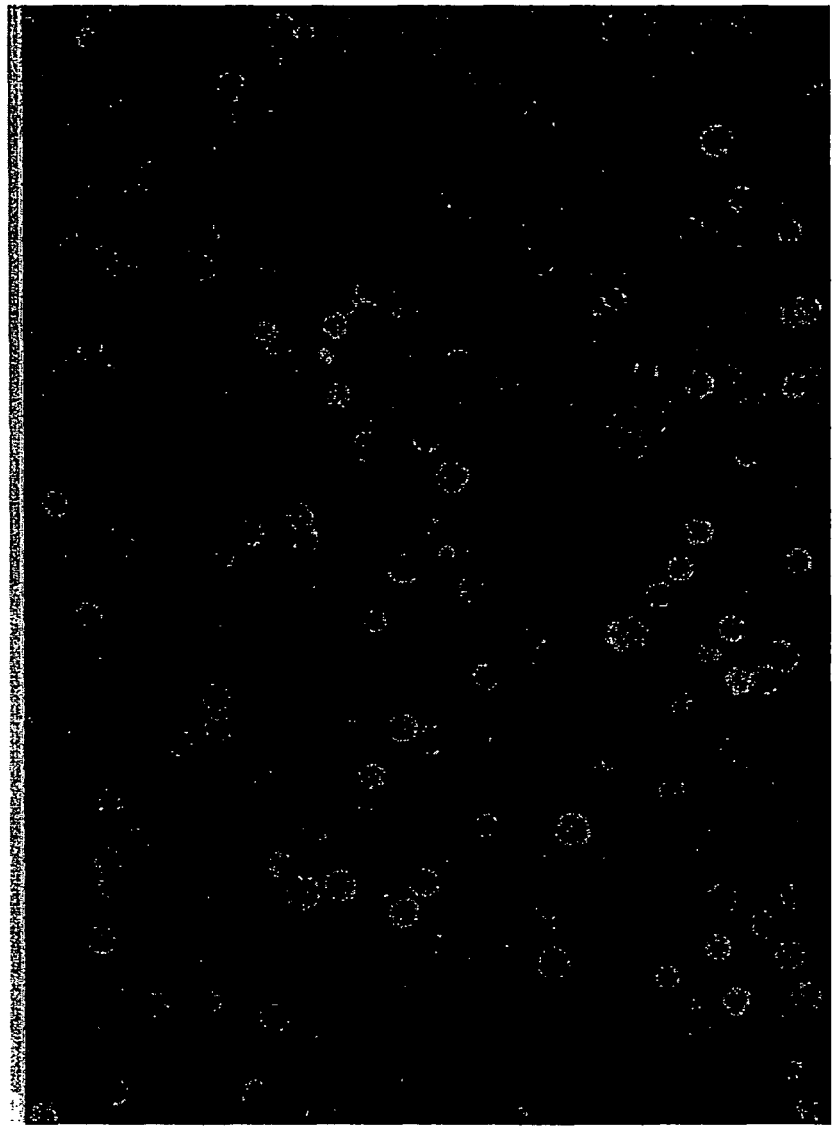
FIG. 1. Indirect immunofluorescence assay showing the reactivity of the antibody preparation C2B8-25t to CD20 positive SB cells. Negative controls, including the HSB CD20 negative cell line and cells treated only with the secondary FITC-conjugated anti-human Fc polyclonal antibody are not shown.

Terms are used herein as generally used in the art, unless otherwise defined as follows:

As used herein, the term antibody is intended to include whole antibody molecules, antibody fragments, or fusionproteins that include a region equivalent to the Fc region of an immunoglobulin.

As used herein, the term region equivalent to the Fc region of an immunoglobulin is intended to include naturally occurring allelic variants of the Fc region of an immunoglobulin as well as variants having alterations which produce substitutions, additions, or deletions but which do not decrease substantially the ability of the immunoglobulin to mediate antibody dependent cellular cytotoxicity. For example, one or more amino acids can be deleted from the N-terminus or C-terminus of the Fc region of an immunoglobulin without substantial loss of biological function. Such variants can be selected according to general rules known in the art so as to have minimal effect on activity. (See, e.g., Bowie, J. U. et al., *Science* 247:1306-10 (1990).

As used herein, the term glycoprotein-modifying glycosyl transferase refers to β(1,4)-N-acetylglucosaminyltransferase III (GnTIII).

As used herein, the terms engineer, engineered, engineering and glycosylation engineering are considered to include any manipulation of the glycosylation pattern of a naturally occurring polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation.

As used herein, the term host cell covers any kind of cellular system which can be engineered to generate modified glycoforms of proteins, protein fragments, or peptides of interest, including antibodies and antibody fragments. Typically, the host cells have been manipulated to express optimized levels of GnT III. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, and insect cells, to name only a few, but also cells comprised within a transgenic animal or cultured tissue.

As used herein, the term Fc-mediated cellular cytotoxicity includes antibody-dependent cellular cytotoxicity and cellular cytotoxicity mediated by a soluble Fc-fusion protein containing a human Fc-region. It is an immune mechanism leading to the lysis of "antibody-targeted cells" by "human immune effector cells", wherein:

The "human immune effector cells" are a population of leukocytes that display Fc receptors on their surface through which they bind to the Fc-region of antibodies or of Fc-fusion proteins and perform effector functions. Such a population may include, but is not limited to, peripheral blood mononuclear cells (PBMC) and/or natural killer (NK) cells.

The "antibody-targeted cells" are cells bound by the antibodies or Fc-fusion proteins. The antibodies or Fc fusion-proteins bind to target cells via the protein part N-terminal to the Fc region.

As used herein, the term increased Fc-mediated cellular cytotoxicity is defined as either an increase in the number of "antibody-targeted cells" that are lysed in a given time, at a given concentration of antibody, or of Fc-fusion protein, in the medium surrounding the target cells, by the mechanism of Fc-mediated cellular cytotoxicity defined above, and/or a reduction in the concentration of antibody, or of Fc-fusion protein, in the medium surrounding the target cells, required to achieve the lysis of a given number of "antibody-targeted cells", in a given time, by the mechanism of Fc-mediated cellular cytotoxicity. The increase in Fc-mediated cellular cytotoxicity is relative to the cellular cytotoxicity mediated by the same antibody, or Fc-fusion protein, produced by the same type of host cells, using the same standard production, purification, formulation and storage methods, which are known to those skilled in the art, but that has not been produced by host cells engineered to express the glycosyltransferase GnTIII by the methods described herein.

By antibody having increased antibody dependent cellular cytotoxicity (ADCC) is meant an antibody having increased ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at 5×10$^6$ cells/ml in RPMI cell culture medium;
   ii) the target cells are grown by standard tissue culture methods, harvested from the exponential growth phase with a viability higher than 90%, washed in RPMI cell culture medium, labelled with 100 micro- Curies of $^{51}$Cr, washed twice with cell culture medium, and resuspended in cell culture medium at a density of $10^5$ cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labelled target cells, receive 50 microliters of a 2% (V/V) aqueous solution of non-ionic detergent (Nonidet, Sigma, St. Louis), instead of the antibody solution (point iv above);

vi) for the spontaneous release (SR) controls, 3 additional wells in the plate containing the labelled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector: target cell ratio of 25:1 and the plates are placed in an incubator under 5% $CO_2$ atmosphere at 37° C. for 4 hours;

ix) the cell-free supernatant from each well is harvested and the experimentally released radioactivity (ER) is quantified using a gamma counter;

x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress the glycosyltransferase GnTIII.

As used herein, the term anti-CD20 antibody is intended to mean an antibody which specifically recognizes a cell surface non-glycosylated phosphoprotein of 35,000 Daltons, typically designated as the human B lymphocyte restricted differentiation antigen Bp35, commonly referred to as CD20.

Identification and Generation of Nucleic Acids Encoding a Protein for which Modification of the Glycosylation Pattern is Desired The present invention provides methods for the generation and use of host cell systems for the production of glycoforms of antibodies or antibody fragments or fusion proteins which include antibody fragments with increased antibody-dependent cellular cytotoxicity. Identification of target epitopes and generation of antibodies having potential therapeutic value, for which modification of the glycosylation pattern is desired, and isolation of their respective coding nucleic acid sequence is within the scope of the invention.

Various procedures known in the art may be used for the production of antibodies to target epitopes of interest. Such antibodies include but are not limited to polyclonal, monoclonal, chimeric, single chain, Fab fragments and fragments produced by an Fab expression library. Such antibodies may be useful, e.g., as diagnostic or therapeutic agents. As therapeutic agents, neutralizing antibodies, i.e., those which compete for binding with a ligand, substrate or adapter molecule, are of especially preferred interest.

For the production of antibodies, various host animals are immunized by injection with the target protein of interest including, but not limited to, rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, saponin, oil emulsions, keyhole limpet hemocyanin, dinitrophenol, and potentially useful human adjuvants such as BCG (bacille Calmette-Guerin) and *Corynebacterium parvum*.

Monoclonal antibodies to the target of interest may be prepared using any technique which provides for the production of antibody molecules by continuous cell lines in culture. These include, but are not limited to, the hybridoma technique originally described by Kohler and Milstein, *Nature* 256:495-97 (1975), the human B-cell hybridoma technique (Kosbor et al., *Immunology Today* 4:72 (1983); Cote et al., *Proc. Natl. Acad. Sci. U.S.A.* 80:2026-30 (1983) and the EBV-hybridoma technique (Cole et al., *Monoclonal Antibodies and Cancer Therapy* 77-96 (Alan R. Liss, Inc., 1985)). In addition, techniques developed for the production of "chimeric antibodies" (Morrison et al., *Proc. Natl. Acad. Sci. U.S.A.* 81:6851-55 (1984); Neuberger et al., *Nature* 312:604-08 (1984); Takeda et al., *Nature* 314:452-54 (1985) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies having a desired specificity.

Antibody fragments which contain specific binding sites of the target protein of interest may be generated by known techniques. For example, such fragments include, but are not limited to, F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., *Science* 246:1275-81 (1989) to allow rapid and easy identification of monoclonal Fab fragments with the desired specificity to the target protein of interest.

Once an antibody or antibody fragment has been identified for which modification in the glycosylation pattern are desired, the coding nucleic acid sequence is identified and isolated using techniques well known in the art.

a. Generation of Cell Lines for the Production of Proteins with Altered Glycosylation Pattern The present invention provides host cell expression systems for the generation of proteins having modified glycosylation patterns. In particular, the present invention provides host cell systems for the generation of glycoforms of proteins having an improved therapeutic value. Therefore, the invention provides host cell expression systems selected or engineered to increase the expression of a glycoprotein-modifying glycosyltransferase, namely β(1,4)-N-acetylglucosaminyltransferase III (GnTIII). Specifically, such host cell expression systems may be engineered to comprise a recombinant nucleic acid molecule encoding GnTIII, operatively linked to a constitutive or regulated promoter system. Alternatively, host cell expression systems may be employed that naturally produce, are induced to produce, and/or are selected to produce GnTIII.

In one specific embodiment, the present invention provides a host cell that has been engineered to express at least one nucleic acid encoding GnTIII. In one aspect, the host cell is transformed or transfected with a nucleic acid molecule comprising at least one gene encoding GnTIII. In an alternate aspect, the host cell has been engineered and/or selected in such way that endogenous GnTIII is activated. For example, the host cell may be selected to carry a mutation triggering expression of endogenous GnTIII. In one specific embodiment, the host cell is a CHO lec10 mutant. Alternatively, the host cell may be engineered such that endogenous GnTIII is activated. In again another alternative, the host cell is engineered such that endogenous GnTIII has been activated by insertion of a constitutive promoter element, a transposon, or a retroviral element into the host cell chromosome.

Generally, any type of cultured cell line can be used as a background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, yeast cells, or insect cells are used as the background cell line to generate the engineered host cells of the invention.

The invention is contemplated to encompass any engineered host cells expressing GnTIII as defined herein.

One or several nucleic acids encoding GnTIII may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding GnTIII are comprised within the host cell system, some of them may be expressed under the control of a constitutive promoter, while others are expressed under the control of a regulated promoter. The maximal expression level is considered to be the highest possible level of stable GnTIII expression that does not have a significant adverse effect on cell growth rate, and will be determined using routine experimentation. Expression levels are determined by methods generally known in the art, including Western blot analysis using a GnTIII specific antibody, Northern blot analysis using a GnTIII specific nucleic acid probe, or measurement of enzymatic activity. Alternatively, a lectin may be employed which binds to biosynthetic products of the GnTIII, for example, $E_4$-PHA lectin. In a further alternative, the nucleic acid may be operatively linked to a reporter gene; the expression levels of the GnTIII are determined by measuring a signal correlated with the expression level of the reporter gene. The reporter gene may transcribed together with the nucleic acid(s) encoding said GnTIII as a single mRNA molecule; their respective coding sequences may be linked either by an internal ribosome entry site (IRES) or by a cap-independent translation enhancer (CITE). The reporter gene may be translated together with at least one nucleic acid encoding said GnTIII such that a single polypeptide chain is formed. The nucleic acid encoding the GnTIII may be operatively linked to the reporter gene under the control of a single promoter, such that the nucleic acid encoding the GnTIII and the reporter gene are transcribed into an RNA molecule which is alternatively spliced into two separate messenger RNA (mRNA) molecules; one of the resulting mRNAs is translated into said reporter protein, and the other is translated into said GnTIII.

If several different nucleic acids encoding GnTIII are expressed, they may be arranged in such way that they are transcribed as one or as several mRNA molecules. If they are transcribed as a single mRNA molecule, their respective coding sequences may be linked either by an internal ribosome entry site (IRES) or by a cap-independent translation enhancer (CITE). They may be transcribed from a single promoter into an RNA molecule which is alternatively spliced into several separate messenger RNA (mRNA) molecules, which then are each translated into their respective encoded GnTIII.

In other embodiments, the present invention provides host cell expression systems for the generation of therapeutic antibodies, having an increased antibody-dependent cellular cytotoxicity, and cells which display the IgG Fc region on the surface to promote Fc-mediated cytotoxicity. Generally, the host cell expression systems have been engineered and/or selected to express nucleic acids encoding the antibody for which the production of altered glycoforms is desired, along with at least one nucleic acid encoding GnTIII. In one embodiment, the host cell system is transfected with at least one gene encoding GnTIII. Typically, the transfected cells are selected to identify and isolate clones that stably express the GnTIII. In another embodiment, the host cell has been selected for expression of endogenous GnTIII. For example, cells may be selected carrying mutations which trigger expression of otherwise silent GnTIII. For example, CHO cells are known to carry a silent GnT III gene that is active in certain mutants, e.g., in the mutant Lec10. Furthermore, methods known in the art may be used to activate silent GnTIII, including the insertion of a regulated or constitutive promoter, the use of transposons, retroviral elements, etc. Also the use of gene knockout technologies or the use of ribozyme methods may be used to tailor the host cell's GnTIII expression level, and is therefore within the scope of the invention.

Any type of cultured cell line can be used as background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, yeast cell, or insect cells may be used. Typically, such cell lines are engineered to further comprise at least one transfected nucleic acid encoding a whole antibody molecule, an antibody fragment, or a fusion protein that includes a region equivalent to the Fc region of an immunoglobulin. In an alternative embodiment, a hybridoma cell line expressing a particular antibody of interest is used as background cell line to generate the engineered host cells of the invention.

Typically, at least one nucleic acid in the host cell system encodes GnT III.

One or several nucleic acids encoding GnTIII may be expressed under the control of a constitutive promoter, or alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding GnTIII are comprised within the host cell system, some of them may be expressed under the control of a constitutive promoter, while others are expressed under the control of a regulated promoter. The maximal expression level is considered to be the highest possible level of stable GnTIII expression that does not have a significant adverse effect on cell growth rate, and will be determined using routine experimentation. Expression levels are determined by methods generally known in the art, including Western blot analysis using a GnTIII specific antibody, Northern blot analysis using a GnTIII specific nucleic acid probe, or measurement of GnTIII enzymatic activity. Alternatively, a lectin may be employed which binds to biosynthetic products of GnTIII, for example, $E_4$-PHA lectin. In a further alternative, the nucleic acid may be operatively linked to a reporter gene; the expression levels of the glycoprotein-modifying glycosyl transferase are determined by measuring a signal correlated with the expression level of the reporter gene. The reporter gene may transcribed together with the nucleic acid(s) encoding said glycoprotein-modifying glycosyl transferase as a single mRNA molecule; their respective coding sequences may be linked either by an internal ribosome entry site (IRES) or by a cap-independent translation enhancer (CITE). The reporter gene may be translated together with at least one nucleic acid encoding GnTIII such that a single polypeptide chain is formed. The nucleic acid encoding the GnTIII may be operatively linked to the reporter gene under the control of a single promoter, such that the nucleic acid encoding the GnTIII and the reporter gene are transcribed into an RNA molecule which is alternatively spliced into two separate messenger RNA (mRNA) molecules; one of the resulting mRNAs is translated into said reporter protein, and the other is translated into said GnTIII.

If several different nucleic acids encoding a GnTIII are expressed, they may be arranged in such way that they are transcribed as one or as several mRNA molecules. If they are transcribed as single mRNA molecule, their respective coding sequences may be linked either by an internal ribosome entry site (IRES) or by a cap-independent translation enhancer (CITE). They may be transcribed from a single promoter into an RNA molecule which is alternatively spliced into several separate messenger RNA (mRNA) molecules, which then are each translated into their respective encoded GnTIII.

i. Expression Systems

Methods which are well known to those skilled in the art can be used to construct expression vectors containing the coding sequence of the protein of interest and the coding sequence of the GnTIII and appropriate transcriptional/translational control signals. These methods include in vitro recombinant DNA techniques, synthetic techniques and in vivo recombination/genetic recombination. See, for example, the techniques described in Maniatis et al., Molecular Cloning A Laboratory Manual, Cold Spring Harbor Laboratory, N.Y. (1989) and Ausubel et al., Current Protocols in Molecular Biology, Greene Publishing Associates and Wiley Interscience, N.Y. (1989).

A variety of host-expression vector systems may be utilized to express the coding sequence of the protein of interest and the coding sequence of the GnTIII. Preferably, mammalian cells are used as host cell systems transfected with recombinant plasmid DNA or cosmid DNA expression vectors containing the coding sequence of the protein of interest and the coding sequence of the GnTIII. Most preferably, CHO cells, BHK cells, NS0 cells, SP2/0 cells, YO myeloma cells, P3X63 mouse myeloma cells, PER cells, PER.C6 cells or hybridoma cells, yeast cells, or insect cells are used as host cell system. In alternate embodiments, other eukaryotic host cell systems may be contemplated, including, yeast cells transformed with recombinant yeast expression vectors containing the coding sequence of the protein of interest and the coding sequence of the GnTIII; insect cell systems infected with recombinant virus expression vectors (e.g., baculovirus) containing the coding sequence of the protein of interest and the coding sequence of the GnTIII; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the protein of interest and the coding sequence of the GnTIII; or animal cell systems infected with recombinant virus expression vectors (e.g., adenovirus, vaccinia virus) including cell lines engineered to contain multiple copies of the DNA encoding the protein of interest and the coding sequence of the GnTIII either stably amplified (CHO/dhfr) or unstably amplified in double-minute chromosomes (e.g., murine cell lines).

For the methods of this invention, stable expression is generally preferred to transient expression because it typically achieves more reproducible results and also is more amenable to large scale production. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:2026 (1962)), and adenine phosphoribosyltransferase (Lowy et al., *Cell* 22:817 (1980)) genes, which can be employed in tk⁻, hgprt⁻ or aprt⁻ cells, respectively. Also, antimetabolite resistance can be used as the basis of selection for dhfr, which confers resistance to methotrexate (Wigler et al., *Natl. Acad. Sci. USA* 77:3567 (1989); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Colberre-Garapin et al., *J. Mol. Biol.* 150:1 (1981)); and hygro, which confers resistance to hygromycin (Santerre et al., *Gene* 30:147 (1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047 (1988)); the glutamine synthase system; and ODC (ornithine decarboxylase) which confers resistance to the ornithine decarboxylase inhibitor, 2-(difluoromethyl)-DL-ornithine, DFMO (McConlogue, in: *Current Communications in Molecular Biology*, Cold Spring Harbor Laboratory ed. (1987)).

ii. Identification Of Transfectants or Transformants that Express the Protein Having a Modified Glycosylation Pattern The host cells which contain the coding sequence and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of the protein of interest and the coding sequence of the GnTIII inserted in the expression vector can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the protein of interest and the coding sequence of the GnTIII are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the protein of interest and the coding sequence of the GnTIII.

In the third approach, transcriptional activity for the coding region of the protein of interest and the coding sequence of the GnTIII can be assessed by hybridization assays. For example, RNA can be isolated and analyzed by Northern blot using a probe homologous to the coding sequences of the protein of interest and the coding sequence of the GnTIII or particular portions thereof. Alternatively, total nucleic acids of the host cell may be extracted and assayed for hybridization to such probes.

In the fourth approach, the expression of the protein products of the protein of interest and the coding sequence of the GnTIII can be assessed immunologically, for example by Western blots, immunoassays such as radioimmuno-precipitation, enzyme-linked immunoassays and the like. The ultimate test of the success of the expression system, however, involves the detection of the biologically active gene products.

b. Generation and Use of Proteins and Protein Fragments Having Altered Glycosylation Patterns i. Generation and Use of Antibodies Having Increased Antibody-Dependent Cellular Cytotoxicity In preferred embodiments, the present invention provides glycoforms of antibodies and antibody fragments having increased antibody-dependent cellular cytotoxicity.

Clinical trials of unconjugated monoclonal antibodies (mAbs) for the treatment of some types of cancer have recently yielded encouraging results. Dillman, *Cancer Biother. & Radiopharm.* 12:223-25 (1997); Deo et al., *Immunology Today* 18:127 (1997). A chimeric, unconjugated IgG1 has been approved for low-grade or follicular B-cell non-Hodgkin's lymphoma Dillman, *Cancer Biother. & Radiopharm.* 12:223-25 (1997), while another unconjugated mAb, a humanized IgG1 targeting solid breast tumors, has also been showing promising results in phase III clinical trials. Deo et al., *Immunology Today* 18:127 (1997). The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., *Cancer* 80:317-33 (1997); Surfus et al., *J. Immunother.* 19:184-91 (1996). For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., *Cancer* 80:317-33 (1997); Surfus et al., *J. Immunother.* 19:1.84-91 (1996). ADCC, a lytic attack on antibody-targeted cells, is triggered upon binding of leukocyte receptors to the constant region (Fc) of antibodies. Deo et al., *Immunology Today* 18:127 (1997).

A different, but complementary, approach to increase ADCC activity of unconjugated IgG1s is to engineer the Fc region of the antibody to increase its affinity for the lymphocyte receptors (FcγRs). Protein engineering studies have shown that FcγRs interact with the lower hinge region of the IgG CH2 domain. Lund et al., *J. Immunol.* 157:4963-69 (1996). However, FcγR binding also requires the presence of oligosaccharides covalently attached at the conserved Asn 297 in the CH2 region. Lund et al., *J. Immunol.* 157:4963-69 (1996); Wright and Morrison, *Trends Biotech.* 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., *Biochemistry* 36:130-38 (1997), with low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., *J. Immunol.* 157:4963-69 (1996) The removal of terminal galactoses results in approximately a two-fold reduction in ADCC activity, indicating a role for these residues in FcγR receptor binding. Lund et al, *J. Immunol.* 157:4963-69 (1996)

The mouse or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., *Glycobiology* 318:813-22 (1995). In contrast, it was recently observed that a rat myeloma-produced, humanized IgG1 (CAMPATH-1H) carried a bisecting GlcNAc in some of its glycoforms. Lifely et al., *Glycobiology* 318:813-22 (1995). The rat cell-derived antibody reached a similar in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc. Lifely et al., *Glycobiology* 318:813-22 (1995). In the N-linked glycosylation pathway, a bisecting GlcNAc is added by the enzyme β(1,4)-N-acetylglucosaminyltransferase III (GnT III). Schachter, *Biochem. Cell Biol.* 64:163-81 (1986).

The present inventors used a single antibody-producing CHO cell line, that was previously engineered to express, in an externally-regulated fashion, different levels of a cloned GnT III gene. This approach established for the first time a rigorous correlation between expression of GnTIII and the ADCC activity of the modified antibody.

The present inventors previously showed that C2B8 antibody modified according to the disclosed method had an about sixteen-fold higher ADCC activity than the standard, unmodified C2B8 antibody produced under identical cell culture and purification conditions. Briefly, a C2B8 antibody sample expressed in CHO-tTA-C2B8 cells that do not have GnT III expression showed a cytotoxic activity of about 31% (at 1 μg/ml antibody concentration), measured as in vitro lysis of SB cells (CD20+) by human lymphocytes. In contrast, C2B8 antibody derived from a CHO cell culture expressing GnT III at a basal, largely repressed level showed at 1 μg/ml antibody concentration a 33% increase in ADCC activity against the control at the same antibody concentration. Moreover, increasing the expression of GnT III produced a large increase of almost 80% in the maximal ADCC activity (at 1 μg/ml antibody concentration) compared to the control at the same antibody concentration. (See International Publication No. WO 99/54342, the entire contents of which are hereby incorporated by reference.)

Further antibodies of the invention having increased antibody-dependent cellular cytotoxicity include, but are not limited to, anti-human neuroblastoma monoclonal antibody (chCE7) produced by the methods of the invention, a chimeric anti-human renal cell carcinoma monoclonal antibody (ch-G250) produced by the methods of the invention, a humanized anti-HER2 monoclonal antibody (e.g., Trastuzumab (HERCEPTIN)) produced by the methods of the invention, a chimeric anti-human colon, lung, and breast carcinoma monoclonal antibody (ING-1) produced by the methods of the invention, a humanized anti-human 17-1A antigen monoclonal antibody (3622W94) produced by the methods of the invention, a humanized anti-human colorectal tumor antibody (A33) produced by the methods of the invention, an anti-human melanoma antibody (R24) directed against GD3 ganglioside produced by the methods of the invention, and a chimeric anti-human squamous-cell carcinoma monoclonal antibody (SF-25) produced by the methods of the invention, an anti-human small cell lung carcinoma monoclonal antibody (BEC2, ImClone Systems, Merck KgaA) produced by the methods of the invention, an anti-human non-Hodgkin's lymphoma monoclonal antibody (Bexxar (tositumomab, Coulter Pharmaceuticals), Oncolym (Techniclone, Alpha Therapeutic)) produced by the methods of the invention, an anti-human squamous cell head and neck carcinoma monoclonal antibody (C225, ImClone Systems) prepared by the methods of the invention, an anti-human rectal and colon carcinoma monoclonal antibody (Panorex (edrecolomab), Centocor, Glaxo Wellcome) prepared by the methods of the invention, an anti-human ovarian carcinoma monoclonal antibody (Theragyn, Antisoma) produced by the methods of the invention, an anti-human acute myelogenous leukemia carcinoma monoclonal antibody (SmartM195, Protein Design Labs, Kanebo) produced by the methods of the invention, an anti-human malignant glioma monoclonal antibody (Cotara, Techniclone, Cambridge Antibody Technology) produced by the methods of the invention, an anti-human B cell non-Hodgkins lymphoma monoclonal antibody (IDEC-Y2B8, IDEC Pharmaceuticals) produced by the methods of the invention, an anti-human solid tumors monoclonal antibody (CEA-Cide, Immunomedics) produced by the methods of the invention, an anti-human colorectal carcinoma monoclonal antibody (Iodine 131-MN-14, Immunomedics) produced by the methods of the invention, an anti-human ovary, kidney, breast, and prostate carcinoma monoclonal antibody (MDX-210, Medarex, Novartis) produced by the methods of the invention, an anti-human colorectal and pancreas carcinoma monoclonal antibody (TTMA, Pharmacie & Upjohn) produced by the methods of the invention, an anti-human TAG-72 expressing carcinoma monoclonal antibody (MDX-220, Medarex) produced by the methods of the invention, an anti-human EGFr-expressing carcinoma monoclonal antibody (MDX-447) produced by the methods of the invention, Anti-VEGF monoclonal antibody (Genentech) produced by the methods of the invention, an anti-human breast, lung, prostate and pancreas carcinoma and malignant melanoma monoclonal antibody (BrevaRex, AltaRex) produced by the methods of the invention, and an anti-human acute myelogenous leukemia monoclonal antibody (Monoclonal Antibody Conjugate, Immunex) produced by the methods of the invention. In addition, the invention is directed to antibody fragment and fusion proteins comprising a region that is equivalent to the Fc region of immunoglobulins.

ii. Generation and Use of Fusion Proteins Comprising a Region Equivalent to an Fc Region of an Immunoglobulin that Promote Fc-Mediated Cytotoxicity As discussed above, the present invention relates to a method for increasing the ADCC activity of therapeutic antibodies. This is achieved by engineering the glycosylation pattern of the Fc region of such antibodies, in particular by maximizing the proportion of antibody molecules carrying bisected complex oligosaccharides and bisected hybrid oligosaccharides N-linked to the conserved glycosylation sites in their Fc regions. This strategy can be applied to increase Fc-mediated cellular cytotoxicity against undesirable cells mediated by any molecule carrying a region that is an equivalent to the Fc region of an immunoglobulin, not only by therapeutic antibodies, since the changes introduced by the engineering of glycosylation affect only the Fc region and therefore its interactions with the Fc receptors on the surface of effector cells involved in the ADCC mechanism. Fc-containing molecules to which the presently disclosed methods can be applied include, but are not limited to, (a) soluble fusion proteins made of a targeting protein domain fused to the N-terminus of an Fc-region (Chamov and Ashkenazi, *Trends Biotech.* 14: 52(1996) and (b) plasma membrane-anchored fusion proteins made of a type II transmembrane domain that localizes to the plasma membrane fused to the N-terminus of an Fc region (Stabila, P. F., *Nature Biotech.* 16: 1357 (1998)).

In the case of soluble fusion proteins (a) the targeting domain directs binding of the fusion protein to undesirable cells such as cancer cells, i.e., in an analogous fashion to therapeutic antibodies. The application of presently disclosed method to enhance the Fc-mediated cellular cytotoxic activity mediated by these molecules would therefore be identical to the method applied to therapeutic antibodies.

In the case of membrane-anchored fusion proteins (b) the undesirable cells in the body have to express the gene encoding the fusion protein. This can be achieved either by gene therapy approaches, i.e., by transfecting the cells in vivo with a plasmid or viral vector that directs expression of the fusion protein-encoding gene to undesirable cells, or by implantation in the body of cells genetically engineered to express the fusion protein on their surface. The later cells would normally be implanted in the body inside a polymer capsule (encapsulated cell therapy) where they cannot be destroyed by an Fc-mediated cellular cytotoxicity mechanism. However should the capsule device fail and the escaping cells become undesirable, then they can be eliminated by Fc-mediated cellular cytotoxicity. Stabila et al., *Nature Biotech.* 16: 1357

(1998). In this case, the presently disclosed method would be applied either by incorporating into the gene therapy vector an additional gene expression cassette directing adequate or maximal expression levels of GnT III or by engineering the cells to be implanted to express adequate or maximal levels of GnT III. In both cases, the aim of the disclosed method is to increase or maximize the proportion of surface-displayed Fc regions carrying bisected complex oligosaccharides and/or bisected hybrid oligosaccharides.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLE 1

New Versions of the Chimeric Anti-CD20 Antibody IDEC-C2B8 Having Enhanced Antibody-Dependent Cellular Cytotoxicity Obtained by Glycosylation Engineering of an IDEC-CEB8 Producing Cell Line Synthesis of VH and VL coding regions of IDEC-C2B8 and construction of mammalian expression vectors. cDNAs encoding the VH and VL regions of IDEC-C2B8 antibody were assembled from a set of overlapping single-stranded oligonucleotides in a one-step process using PCR (Kobayashi, N., et al., *Biotechniques* 23:500-503(1997)). The original sequence data coding for IDEC-C2B8 VL and VH were obtained from a published international patent application (International Publication Number: WO 94/11026). Assembled VL and VH cDNA fragments were subcloned into pBluescriptIIKS(+), sequenced and directly joined by ligation to the human constant light (Ig κ) and heavy (IgG1) chain cDNAs, respectively, using unique restriction sites introduced at the variable and constant region junctions without altering the original amino acid residue sequence (Umana, P., et al., *Nat Biotechnol.* 17:176-180 (1999); Reff, M. E., et al., *Blood* 83:435-445 (1994)). Each full-length cDNA was separately subcloned into pcDNA3.1(+) (Invitrogen, Leek, The Netherlands) yielding mammalian expression vectors for chimeric C2B8 light (pC2B8L) and heavy (pC2B8H) chains.

Production of IDEC-C2B8 in CHO cells expressing different levels of GnTIII. Establishment of two CHO cell lines, CHO-tet-GnTIII expressing different levels of GnTIII depending on the tetracycline concentration in the culture medium; and CHO-tTA, the parental cell line that does not express GnTIII has been described previously (Umana, P., et al., *Nat Biotechnol.* 17:176-180 (1999); Umana, P., et al., *Biotechnol Bioeng.* 65:542-549 (1999)). Each cell line was cotranfected with vectors pC2B8L, pC2B8H, and pZeoSV2 (+) (for Zeocin resistance; Invitrogen, Leek, The Netherlands) using a calcium phosphate method. Zeocin resistant clones were transferred to a 96-well plate and assayed for IDEC-C2B8 production using an ELISA assay specific for the human constant region (4). Three IDEC-C2B8 samples were obtained from parallel cultures of a selected clone (CHO-tet-GnTIII-C2B8), differing only in the tetracycline concentration added to the medium (25, 50 and 2000 ng/mL respectively). Culture supernatants were harvested in the late exponential phase. An additional antibody sample was obtained from a CHO-tTA-derived clone, CHO-tTA-C2B8, cultured under identical conditions but without adding tetracycline to the medium. Antibody samples were purified from culture medium by protein A affinity chromatography and buffer exchanged to PBS on a cation exchange column as previously described (Umana, P., et al., *Nat Biotechnol.* 17:176-180 (1999)). Antibody concentration was measured using a fluorescence-based kit from Molecular Probes (Leiden, The Netherlands) with Rituximab used as standard.

Indirect immunofluorescence. CD20-positive cells (SB cells; ATCC deposit no. ATCC CCL120) and CD20-negative cells (HSB cells; ATCC deposit no. ATCC CCL120.1) were each incubated for 1 h with 2.5 μg/ml of CHO-tet-GnTIII-derived IDEC-C2B8 antibody in Hank's balanced salt solution (GibcoBRL, Basel, Switzerland) and 2% bovine serum albumin fraction V (Roche Diagnostics, Rotkreuz, Switzerland) (HBSSB). As a negative control HBSSB was used instead of C2B8 antibody. A FITC-conjugated, anti-human Fc polyclonal antibody was used as a secondary antibody (SIGMA, St. Louis) for all samples. Cells were examined using a Leica fluorescence microscope (Wetzlar, Germany).

Oligosaccharide profiling by MALDI/TOF-MS. Neutral, N-linked oligosaccharides were derived from C2B8 antibody samples, MabThera™ (European counterpart of Rituximab; kind gift from R. Stahel, Universitätspital, Switzerland), C2B8-25t, C2B8-50t, C2B-2000t, and C2B8-nt, (100 μg each) as previously described (Umana, P., et al., *Nat Biotechnol.* 17:176-180 (1999)). Briefly, the antibody samples were first treated with *Arthrobacter ureafaciens* sialidase (Oxford Glycosciences, Abingson, UK) to remove any sialic acid monosaccharide residues. Neutral N-linked oligosaccharides were then released from the desialylated antibody samples using peptide-N-glycosidase F (Oxford Glycosciences), purified using micro-columns, and analyzed by MALDI/TOF-MS in an Elite Voyager 400 spectrometer (Perseptive Biosystems, Farmingham, Mass.).

ADCC Activity Assay. Peripheral blood mononuclear cells (PBMC) were separated from heparinated fresh human blood (in all experiments obtained from the same healthy donor) by centrifugation over a Ficoll-Paque (Pharmacia Biotech, Dübendorf, Switzerland) gradient. PBMC (effector) were depleted of monocytes by plastic adherence. CD20-positive SB (target) cells, were labeled for 90 min with 100 μCi $^{51}$Cr (Amersham, Dubendorf, Switzerland) at 37° C., washed twice in RPMI (GibcoBRL, Basel, Switzerland) and resuspended at a concentration of $10^5$ cells/ml. Fifty microliters of C2B8 mAb diluted in RPMI medium was added to 100 μl SB cells (10,000 cells/well) in a 96-well round bottom microtiter plate (Greiner, Langenthal, Switzerland), centrifuged at 50×g for 1 min, and incubated for 1 h at 4° C. Subsequently, 50 μl of effector cell (suspended at $2\times10^7$ cells/ml in RPMI medium) were added to each 96-well yielding a final E:T ratio of 100. Plates were incubated for 4 h at 37° C. and 5% $CO_2$, supernatant was harvested with a Skatron harvesting system (Skatron Instruments, Sterling, Va.) and counted (ER, experimental release) in a Cobra 05005 γ counter (Canberra Packard, Meriden, Conn.). Maximum (MR) and spontaneous (SR) releases were obtained by adding, instead of C2B8 mAb, 100 μl of 1% Nonidet (Sigma, St. Louis) or 100 μl of RPMI medium, respectively, to 100 μl labeled target cells. All data points were performed in triplicate. Specific lysis (%) was calculated with the following formula: (ER−SR)/(MR−SR)×100.

Results and Discussion

Production of IDEC-C2B8 and verification of specific antigen binding. CHO-tet-GnTIII cells, with stable, tetracycline-regulated expression of GnTIII and stable, constitutive expression of IDEC-C2B8, were established and scaled-up for production of a set of antibody samples. During scale-up, parallel cultures from the same clone were grown under three different tetracycline concentrations, 25, 50 and 2000 ng/ml. These levels of tetracycline had previously been shown to result in different levels of GnTIII and bisected oligosaccharides (Umana, P., et al., *Nat Biotechnol.* 17:176-180(1999); Umana, P., et al., *Biotechnol Bioeng.* 65:542-549 (1999)). A C2B8-producing, control cell line that does not express GnTIII was also established and cultured under the same conditions as for the three parallel cultures of CHO-tet-GnTIII. After Protein A-affinity chromatography, mAb purity was estimated to be higher than 95% by SDS-PAGE and Coomassie-blue staining. The samples were named according to the tetracycline concentration added to the culture medium for their production: C2B8-25t, C2B 8-50t, C2B8-2000t and C2B8-nt (i.e., no tetracycline for the non-bisected control). Sample C2B 8-25t showed specific antigen binding by indirect immunofluorescence using CD20-positive and CD20-negative cells (FIG. 1), indicating that the synthesized VL and VH gene fragments were functionally correct.

Oligosaccharide profiling with MALDI/TOF-MS. The glycosylation profile of each antibody sample was analyzed by MALDI/TOF-MS of the released, neutral oligosaccharide mix. In this technique, oligosaccharides of different mass appear as separate peaks in the spectrum and their proportions are quantitatively reflected by the relative peak heights (Harvey, D. J., *Rapid Common Mass Spectrom.* 7:614-619 (1993); Harvey, D. J., et al., *Glycoconj J.* 15:333-338 (1998)). Oligosaccharide structures were assigned to different peaks based on their expected molecular masses, previous structural data for oligosaccharides derived from IgG1 mAbs produced in the same host, and information on the N-linked oligosaccharide biosynthetic pathway.

A clear correlation was found between GnTIII expression levels (i.e., tetracycline concentration) and the amount of bisected oligosaccharides derived from the different antibody samples. As expected, MabThera™ and C2B8-nt, which are derived from hosts that do not express GnTIII, did not carry bisected oligosaccharides (FIGS. 2A and 2B). In contrast, bisected structures amounted up to approximately 35% of the oligosaccharides pool in sample C2B8-2000t, i.e, at a basal level of GnTIII expression. In this case, the main bisected oligosaccharide peaks were of complex type, unequivocally assigned to peaks at m/z 1689 and m/z 1851 (FIG. 2C). The next higher GnTIII expression level, sample C2B8-50t, led to an increase in these peaks (including their associated potassium aducts at m/z 1705 and 1861) of around 20%. This increase was accompanied by a concomitant reduction of their non-bisected counterparts at m/z 1486 and 1648, respectively (FIG. 2D). At the highest GnTIII expression level, sample C2B8-25t, the main substrate for GnTIII, m/z 1486, decreased to almost base-line level, while complex bisected structures (m/z 1689 and 1851) decreased in favor of increases in peaks at m/z 1664, 1810 and 1826 (FIG. 2E). These peaks can be assigned either to bisected hybrid compounds, to galactosylated complex oligosaccharides, or to a mixture of both. Their relative increase, however, is consistent with the accumulation of bisected hybrid compounds, as GnTIII overexpression can divert the biosynthetic flux at early stages of the pathway (see FIGS. 3A and 3B). The amount of bisected oligosaccharide structures (complex and hybrid type) reached approximately 80% for this sample.

Figure 4:
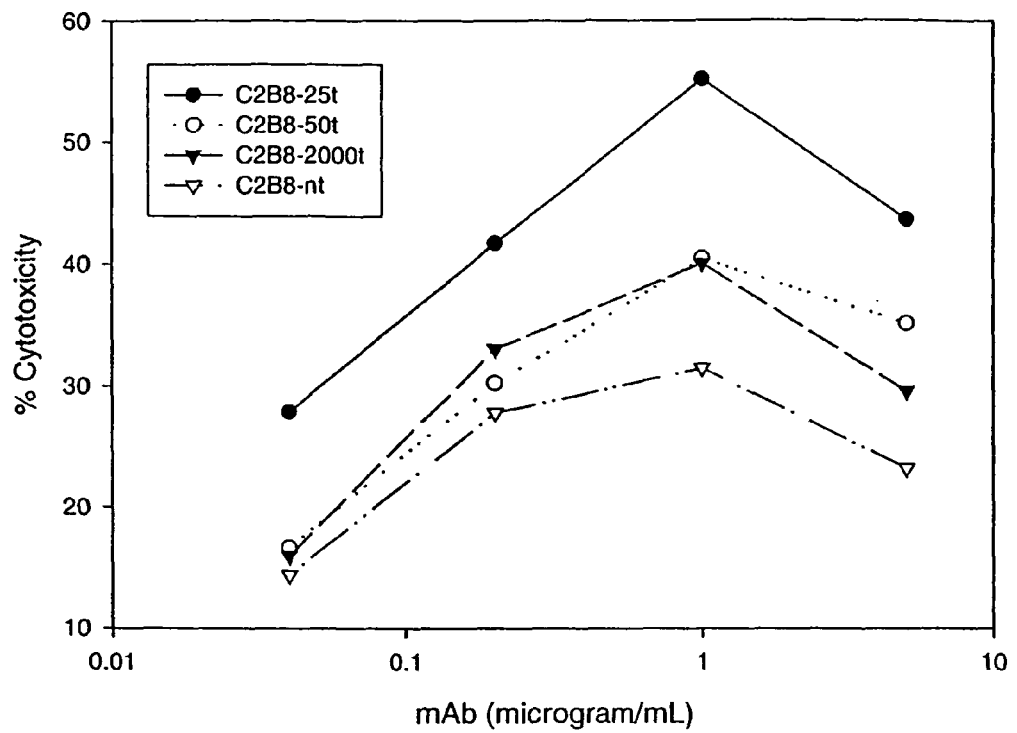
FIGS. 4A and 4B. ADCC activities of Rituximab glycosylation variants. The percentage of cytotoxicity was measured via lysis of $^{51}$Cr labeled CD20-positive SB cells by human lymphocytes (E:T ratio of 100:1) mediated by different mAb concentrations.
Figure 4:
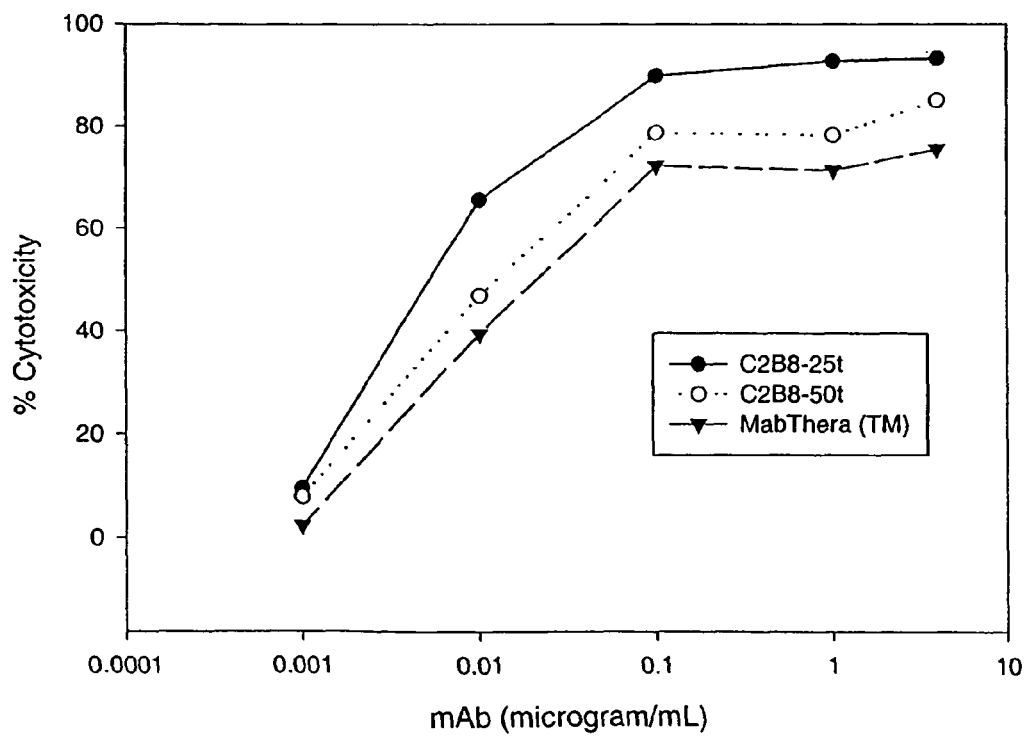

ADCC activity of IDEC-C2B8 glycosylated variants. Different C2B8 mAb glycosylation variants were compared for ADCC activity, measured as in vitro lysis of CD20-positive SB cells. An additional mAb sample, C2B8-nt, derived from the parental cell line lacking GnTIII, was also studied. Sample C2B8-2000t produced at the basal GnTIII expression level and carrying low levels of bisected oligosaccharides was slightly more active than C2B8-nt (FIG. 4A). At the next higher level of GnTIII-expression, sample C2B8-50t carried approximately equal levels of bisected and non-bisected oligosaccharides, but did not mediate significantly higher target-cell lysis. However, at the lowest tetracycline concentration, sample C2B8-25t, which contained up to 80% of bisected oligosaccharide structures, was significantly more active than the rest of the samples in the whole antibody concentration range. It reached the maximal level of ADCC activity of sample C2B8-nt at a 10-fold lower antibody concentration (FIG. 4A). Sample C2B8-25t also showed a significant increase in the maximal ADCC activity with respect to the control (50% vs. 30% lysis).

Samples C2B8-50t and C2B8-25t, bearing the highest proportions of bisected oligosaccharides, were further compared in ADCC activity to Mabthera™, the version of Rituxan™ currently marketed in Europe (FIG. 4B). Sample C2B8-50t showed a slight increase in activity whereas sample C2B8-25t clearly outperformed Mabthera™ at all antibody concentrations. Approximately a five to ten-fold lower concentration of C2B8-25t was required to reach the maximal ADCC activity of Mabthera™, and the maximal activity of C2B8-25t was about 25% higher than that of Mabthera™.

Figure 2:
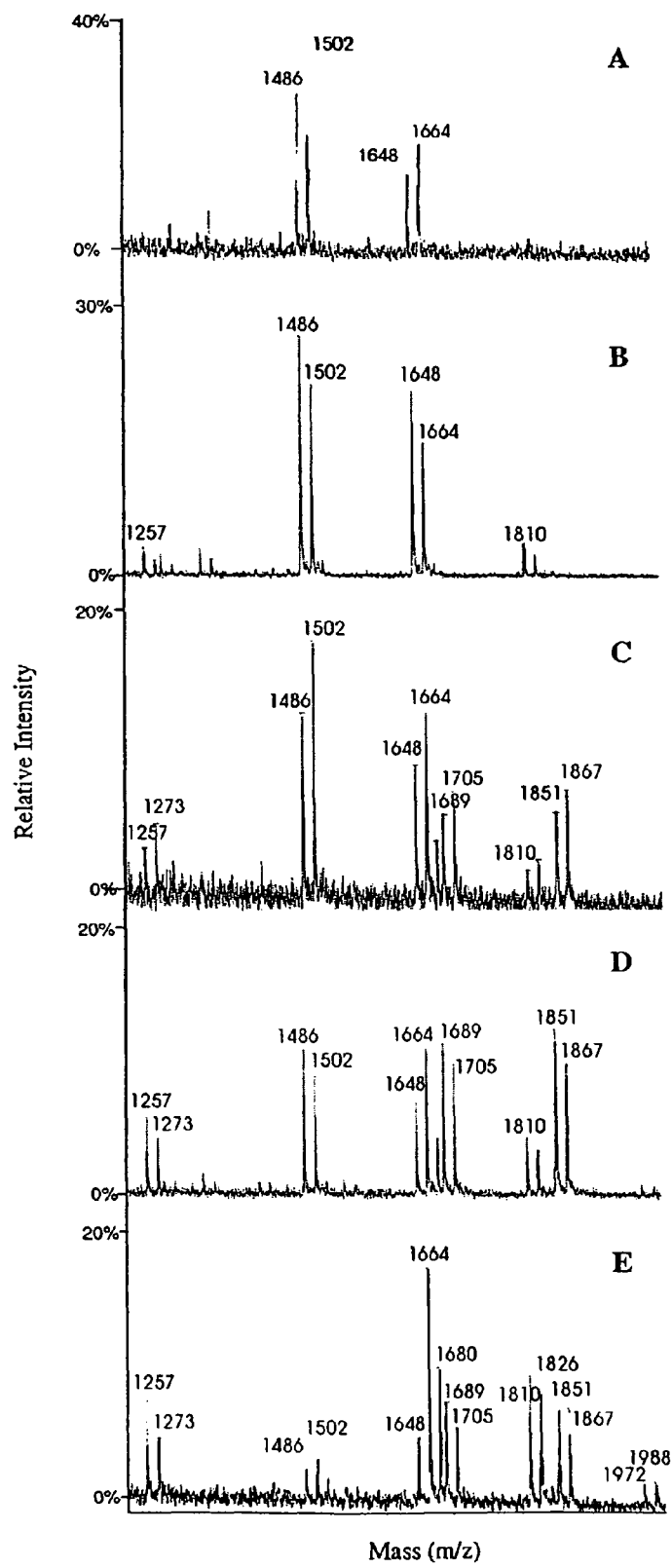
FIG. 2A-2E. MALDI/TOF-MS spectra of the oligosaccharides derived from Mabthera™ (FIG. 2A), C2B8-nt (FIG. 2B), C2B8-2000t (FIG. 2C), C2B8-50t (FIG. 2D), and C2B8-25t (FIG. 2E) antibody samples. Oligosaccharides appear as $[M+Na^+]$ and $[M+K^+]$ ions. Oligosaccharide appearing in the first two spectra were derived from cell cultures that do not express GnTIII, whereas oligosaccharides in C, D, and E were derived from a single cell line expressing GnTIII at different levels (i.e. tetracycline concentrations).
Figure 3:
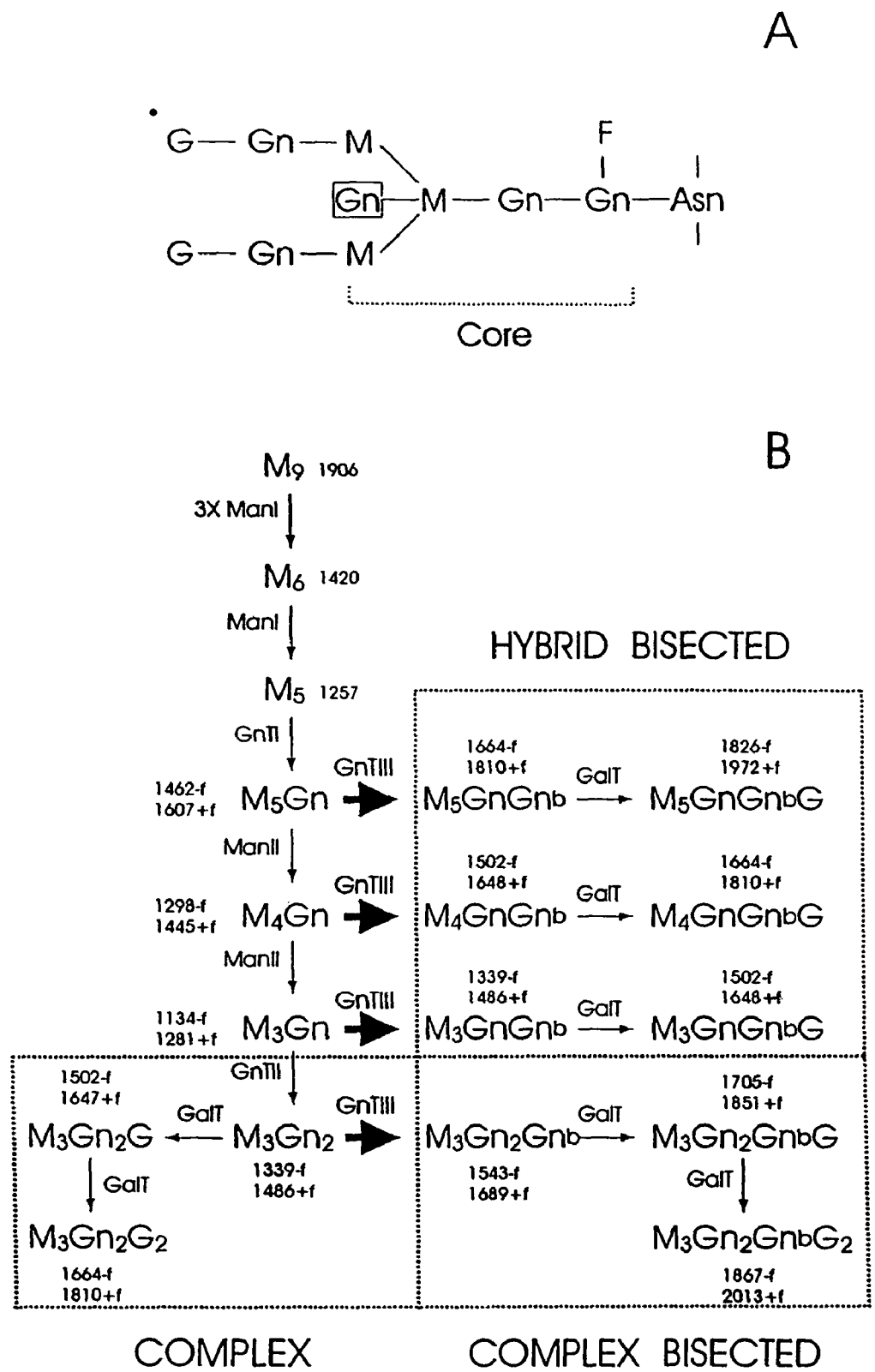
FIGS. 3A and 3B. Illustration of a typical human IgG Fc-associated oligosaccharide structure (A) and partial N-linked glycosylation pathway (B).

These results show that, in general, the in vitro ADCC activity of the C2B8 antibody correlates with the proportion of molecules carrying bisected oligosaccharides in the Fc region. We had previously reported that in the case of chCE7, an antibody with a low baseline level of ADCC activity, significant increases of activity could be obtained by increasing the fraction of bisected oligosaccharides above the levels found in naturally-occurring antibodies (Umana, P., et al., *Nat Biotechnol.* 17:176-180 (1999)). The same is true for the C2B8 mAb, which already has high ADCC activity in the absence of bisected oligosaccharides. In the case of chCE7, however, very large increases of ADCC activity were observed at a level of GnTIII expression where bisected oligosaccharides were predominantly of complex type (Umana, P., et al., *Nat Biotechnol.* 17:176-180 (1999)). For the potent C2B8 mAb, such a large boost in activity was only observed at the highest levels of GnTIII expression studied, where bisected oligosaccharides had shifted mainly to the hybrid type (FIG. 2). For both mAbs, the samples with the highest activities had considerably higher levels of bisected than non-bisected oligosaccharides. Together, these observations indicate that probably both complex and hybrid bisected oligosaccharides are important for ADCC activity.

In both complex and hybrid oligosaccharides, a bisecting GlcNAc leads to a large change in oligosaccharide conformations (Balaji, P. V., et al., *Int. J. Biol. Macromol.* 18:101-114 (1996)). The change occurs in a part of the oligosaccharide that interacts extensively with the polypeptide in the CH2 domain (Jefferis, R., et al., *Immunol Rev.* 163:59-76 (1998)). Since the polypetide is relatively flexible at this location (Jefferis, R., et al., *Immunol Rev.* 163:59-76 (1998)), it is possible that the bisecting N-acetylglucosamine is mediating its biological effects through a conformational change in the Fc region. The potentially altered conformations would already exist in nature, as all serum IgGs carry bisected oligosaccharides. The main difference between the engineered and natural antibodies would be the proportion of molecules displaying the more active conformations.

Various approaches for increasing the activity of unconjugated mAbs are currently under clinical evaluation, including radio-immunotherapy, antibody-dependent enzyme/pro-drugtherapy, immunotoxins and adjuvant therapy with cytokines (Hjelm Skog, A., et al., *Cancer Immunol Immunother.* 48:463-470 (1999); Blakey, D. C., et al., *Cell Biophys.* 25: 175-183 (1994); Wiseman, G. A., et al., *Clin Cancer Res.* 5:3281s-3296s (1999); Hank, J. A., et al., *Cancer Res.* 50:5234-5239 (1990)). These technologies can give large increases in activity, but they can also lead to significantly higher side effects, elevated production costs and complex logistics from production to administration to patients when compared to unconjugated mAbs. The technology presented here offers an alternative way to obtain increases in potency while maintaining a simple production process, and should be applicable to many unconjugated mAbs.

EXAMPLE 2

New Versions of the Anti-Renal Cell Carcinoma Antibody chG250 Having Enhanced Antibody-Dependent Cellular Cytotoxicity Obtained by Glycosylation Engineering of a chG250 Producing Cell Line 1. Cell Culture SP2/0 mouse myeloma cells producing chG250 chimeric mAb (wt-chG250-SP2/0 cells) were grown in standard cell culture medium supplemented with 1:100 (v/v) penicillin/streptomycin/antimycotic solution (SIGMA, Buchs, Switzerland). Cells were cultured at 37° C. in a 5% $CO_2$ humidified atmosphere in Tissue Culture Flasks. Medium was changed each 3-4 days. Cells were frozen in culture medium containing 10% DMSO.

2. Generation of SP2/0 Cells with pGnTIII-puro Expression wt-chG250-SP2/O myeloma cells were transfected by electroporation with a vector for constitutive expression of GnTIII operatively linked via an IRES to a puromycin resistance gene. 24 hours before electroporation culture medium was changed and cells were seeded at $5 \times 10^5$ cells/ml. Seven million cells were centrifuged for 4 min at 1300 rpm at 4° C. Cells were washed with 3 mL new medium and centrifuged again. Cells were resuspended in a volume of 0.3-0.5 ml of reaction mix, containing 1.25% (v/v) DMSO and 20-30 µg DNA in culture medium. The electroporation mix was then transferred to a 0.4 cm cuvette and pulsed at low voltage (250-300V) and high capacitance (960 µF) using Gene Pulser from Bio Rad. After electroporation cells were quickly transferred to 6 mL 1.25% (v/v) DMSO culture medium in a T25 culture flask and incubated at 37° C. Stable integrants were selected by applying 2 µg/mL puromycin to the medium two days after electroporation. After 2-3 weeks a stable, puromycin-resitant mixed population was obtained. Single-cell derived clones were obtained via FACS and were subsequently expanded and maintained under puromycin selection.

3. Western Blot

Figure 5:
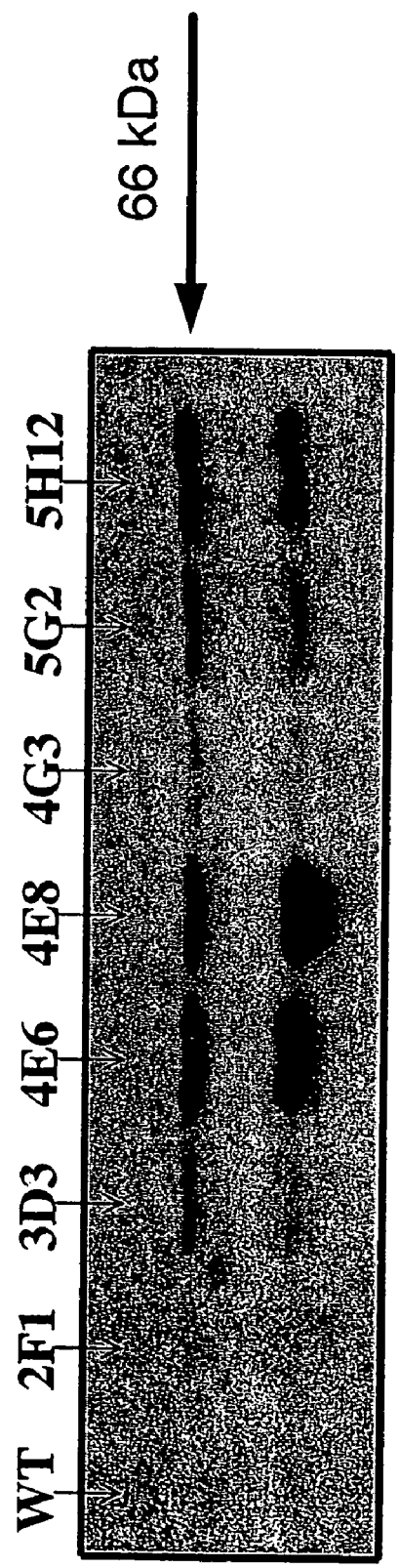
FIG. 5. Western blot analysis of the seven GnTIII expressing clones and the wild type. 30 µg of each sample were loaded on a 8.75% SDS gel, transferred to a PVDF membrane and probed with the anti-c-myc monoclonal antibody (9E10). WT refers to wt-chG250-SP2/0 cells.

Puromycin-resistant clones were screened for GnTIII expression by Western blotting. The Western blots clearly showed that clones 5H12, 4E6 and 4E8 were expressing the highest levels of GnTIII. 5G2 also showed a GnTIII band of middle intensity, whereas 2F1, 3D3 and 4G3 had the lowest band intensities, therefore expressing lower amounts of GnTIII (FIG. 5).

Figure 6:
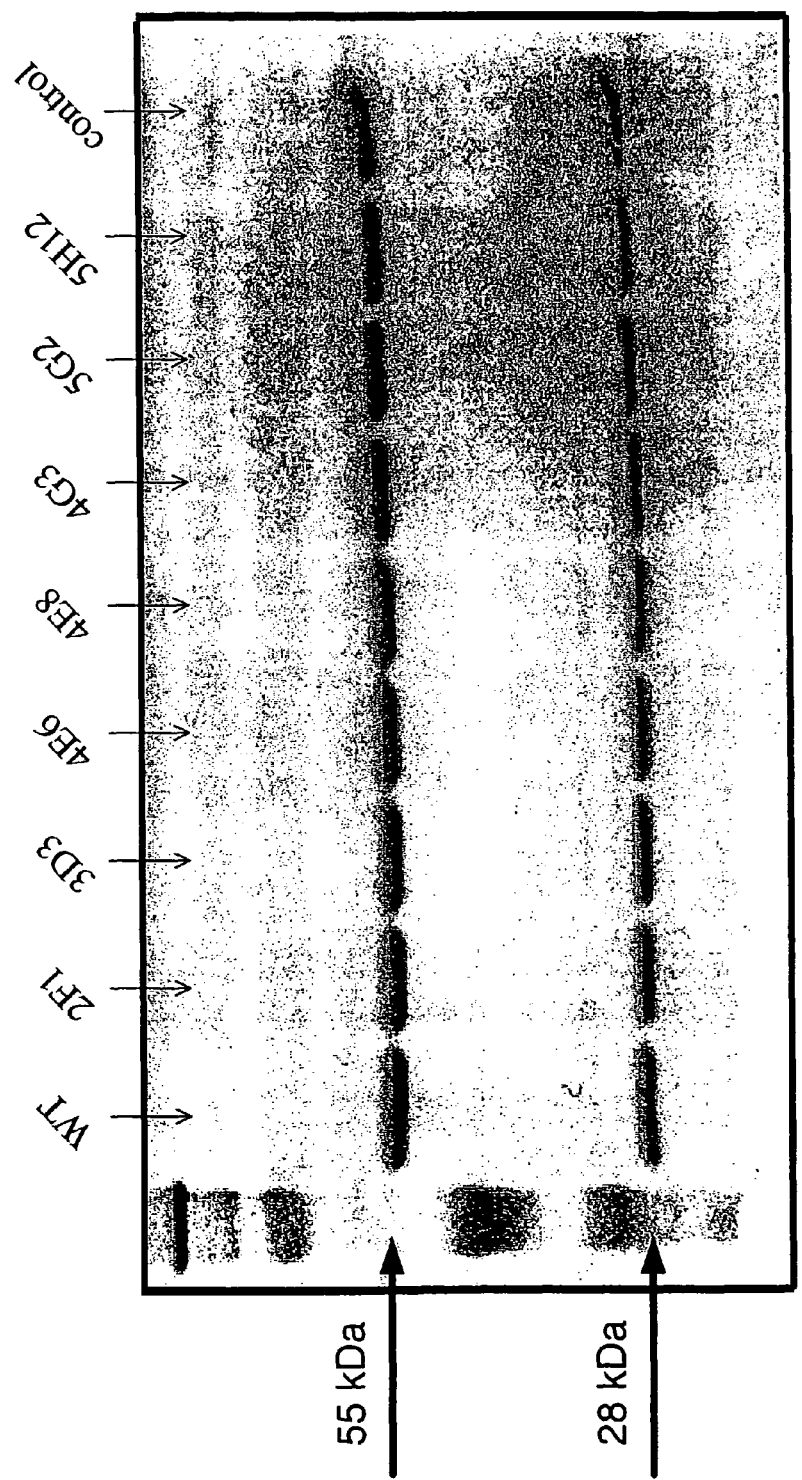
FIG. 6. SDS polyacrylamide gel electrophoresis of resolved purified antibody samples.

4. Production and Purification of chG250 Monoclonal Antibody from Seven GnTIII-Expressing Clones Including Wild Type Clones 2F1, 3D3, 4E6, 4E8, 4G3, 5G2, 5H12 and the wild type (wt-chG250-SP2/0 cells) were seeded at $3 \times 10^5$ cells/mL in a total volume of 130 ml culture medium, and cultivated in single Triple-flasks. Cells used for seeding were all in full exponential growth phase, therefore cells were considered to be at the same growth state when the production batches started. Cells were cultivated for 4 days. Supernatants containing the antibody were collected in the late exponential growth phase to ensure reproducibility. The chG250 monoclonal antibody was purified in two chromatographic steps. Culture supernatants containing the chG250 monoclonal antibody derived from each batch were first purified using a HiTrap Protein A affinity chromatography. Protein A is highly specific for the human IgG $F_c$ region. Pooled samples from the protein A eluate were buffer exchanged to PBS by cation-exchange chromatography on a Resource S 1 ml column (Amersham Pharmacia Biotech). Final purity was judged to be higher than 95% from SDS-staining and Coomassie blue staining (FIG. 6). The concentration of each sample was determined with a standard calibration curve using wild type antibody with known concentration.

5. Oligosaccharide Profiling of mAb Preparations Derived from the Seven Clones Expressing Different GnTIII Levels Oligosaccharide profiles were obtained by matrix-assisted laser desorption/ionization time of flight mass spectrometry (MALDI/TOF-MS), which accurately provides the molecular masses of the different oligosaccharide structures. This technique allows a quantitative analysis of proportions between different oligosaccharide structures within a mixture. Neutral oligosaccharides appeared predominantly as [M+Na$^+$] ions, however sometimes they were accompanied by smaller [M+K$^+$] ions, leading to an increase in mass of m/z of 16. The percentage of the structure appearing as potassium ion adducts depends on the content of the matrix and may thus vary between samples. A mixture of neutral N-linked oligosaccharides derived from each antibody preparation was analyzed using a 2,5-dehydrobenzoic acid (2,5-DHB) as matrix. Some of the peaks in the spectra were unequivocally assigned to specific oligosaccharide structures, because of known monosaccharide composition and unique mass. However, sometimes multiple structures could be assigned to a particular mass. MALDI enables the determination of the mass and cannot distinguish between isomers. Knowledge of the biosynthetic pathway and previous structural data enable, in most cases, the assignment of an oligosaccharide structure to a peak in the spectrum.

Figure 7A:
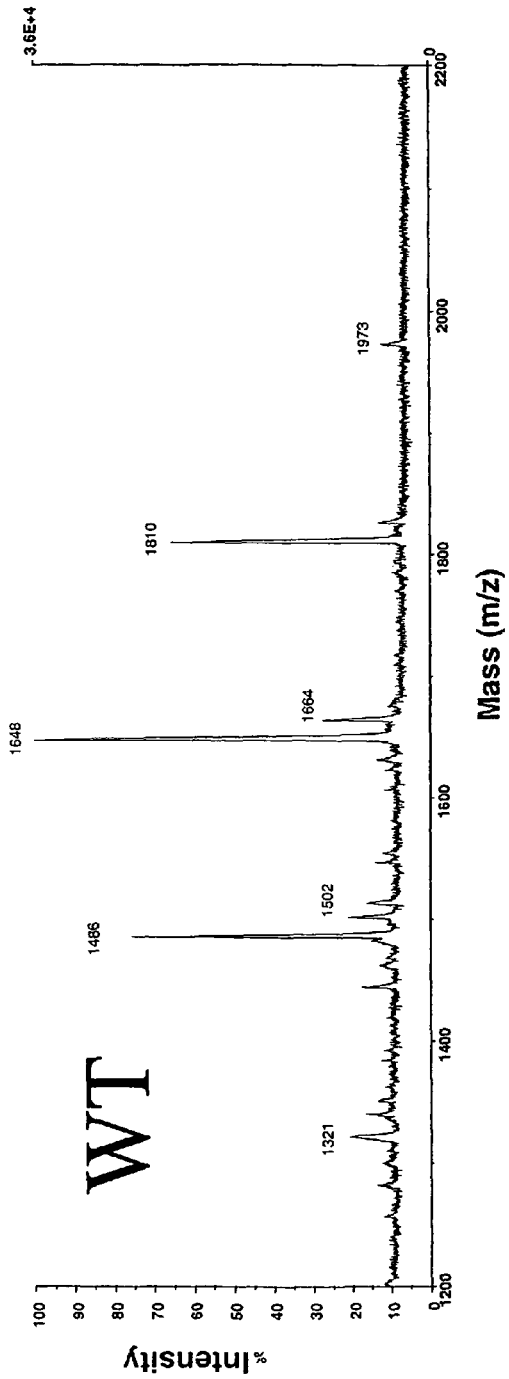
FIG. 7A-7D. MALDI/TOF-MS spectra of neutral oligosaccharide mixtures from chG250 mAb samples produced by clones expressing different GnTIII levels and wt-chG250-SP2/0 cells: WT (FIG. 7A), 2F1 (FIG. 7B), 3D3 (FIG. 7C), 4E6 (FIG. 7D).
Figure 7B:
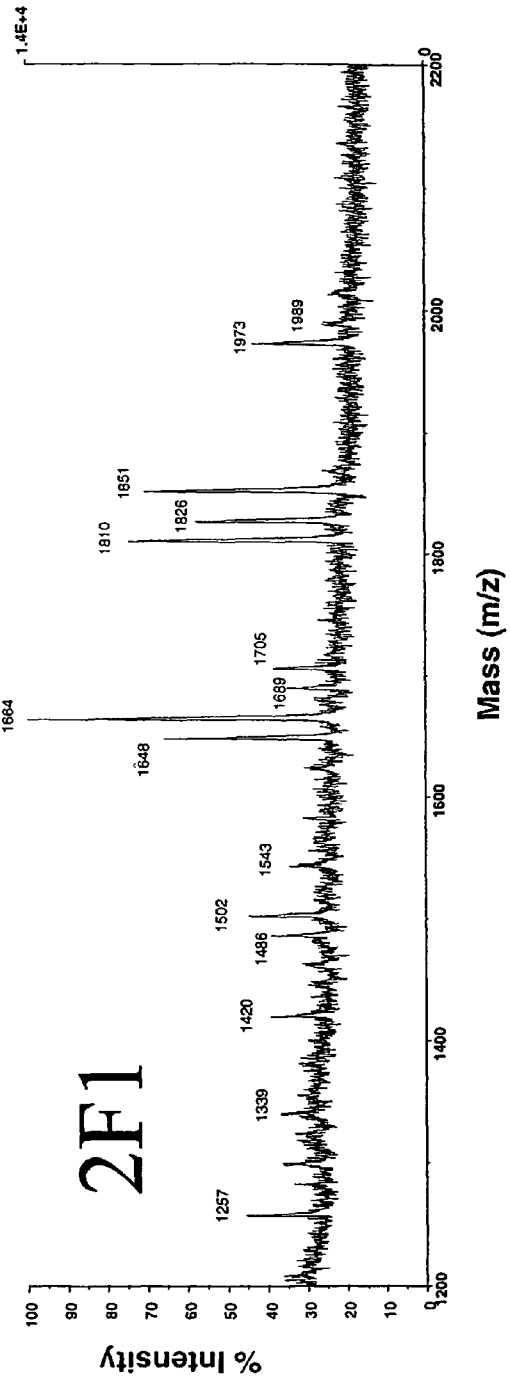
Figure 7C:
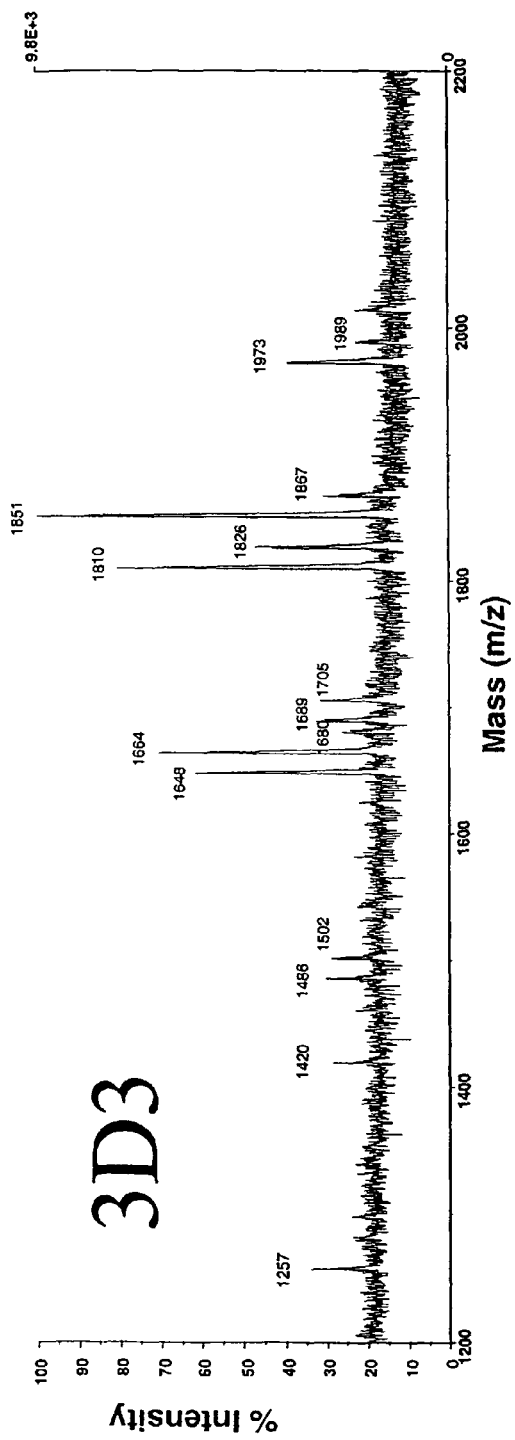
Figure 7D:
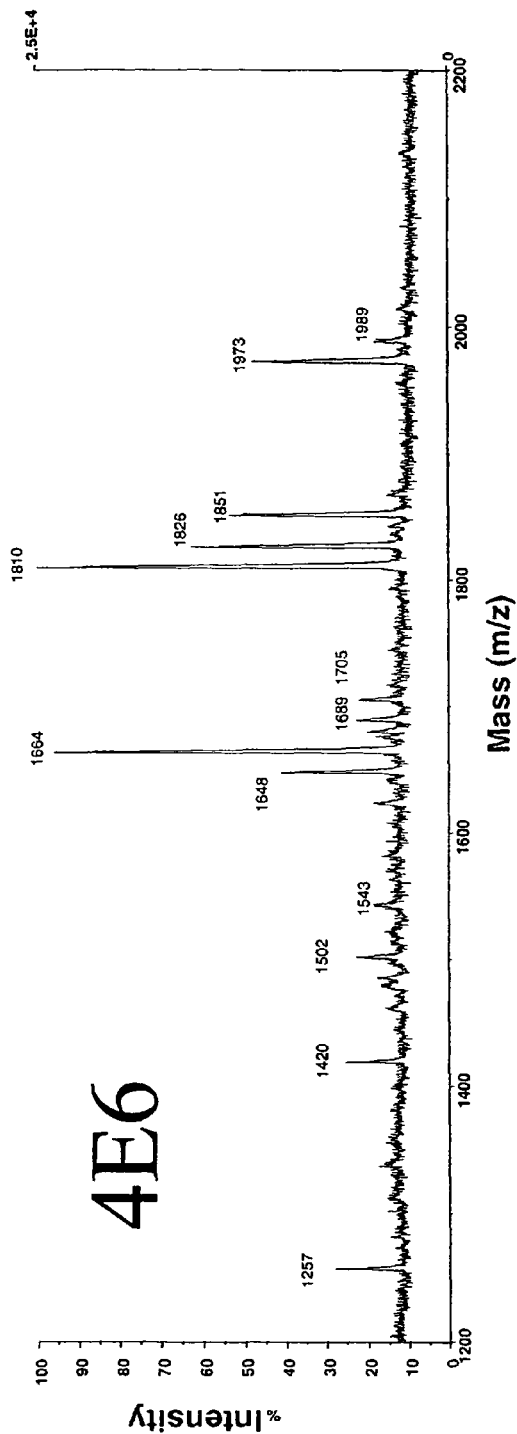
Figure 8A:
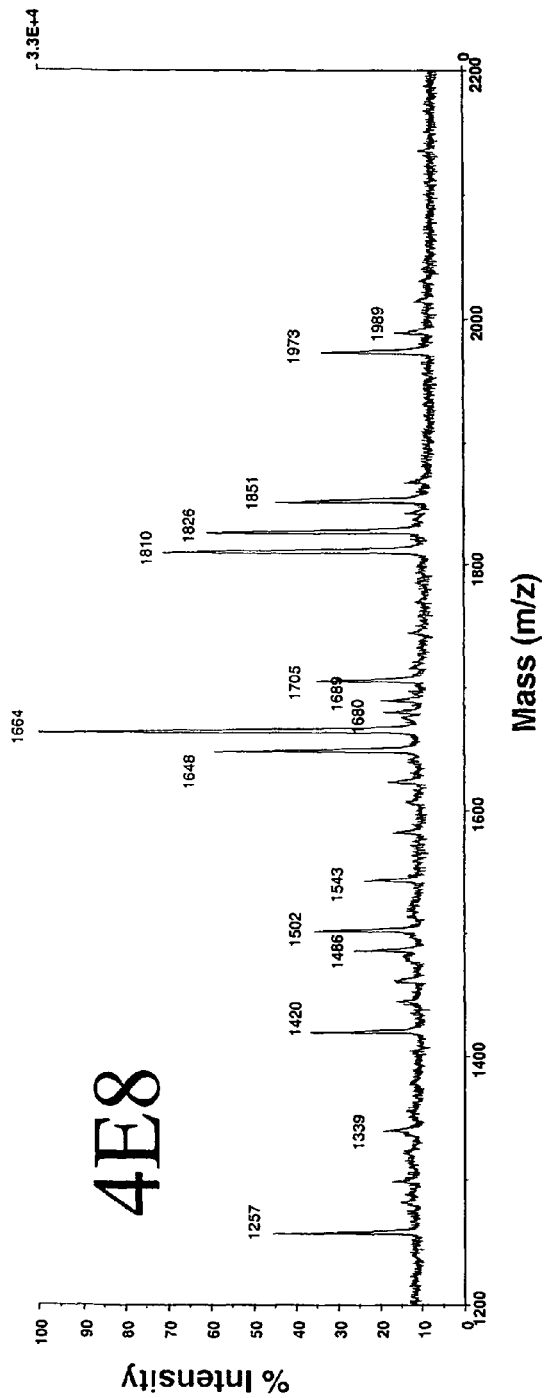
FIG. 8A-8D. MALDI/TOF-MS spectra of neutral oligosaccharide mixtures from chG250 mAb samples produced by clones expressing different GnTIII levels: 4E8, (FIG. 8A); 5G2, (FIG. 8B); 4G3, (FIG. 8C); 5H12, (FIG. 8D).
Figure 8B:
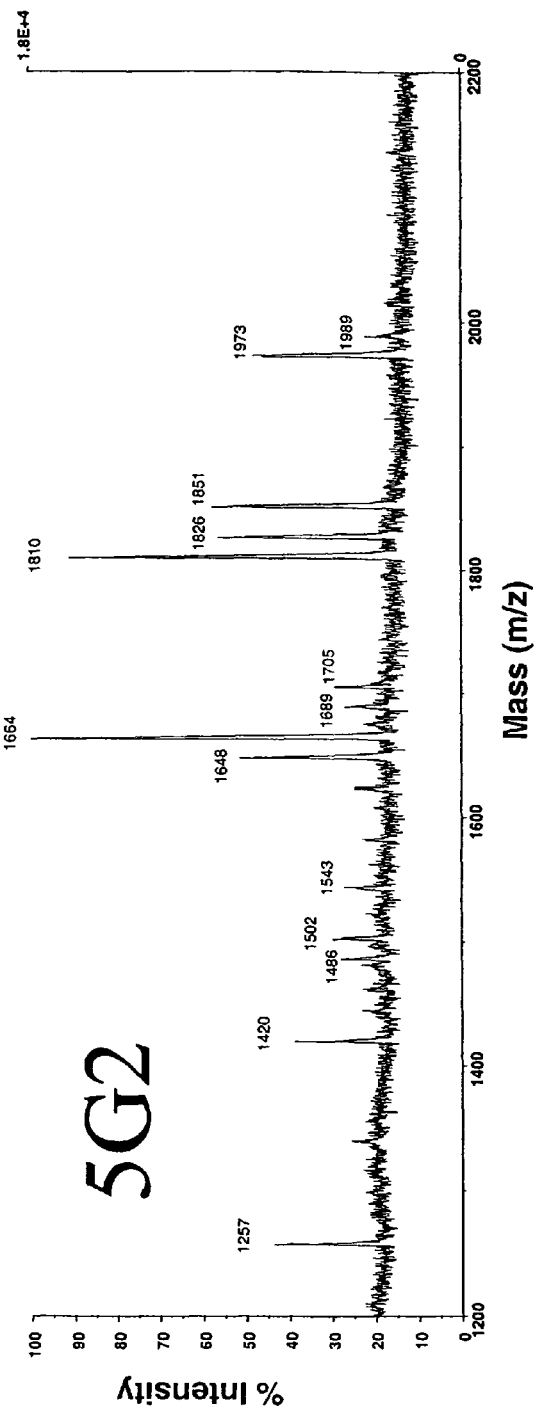
Figure 8C:
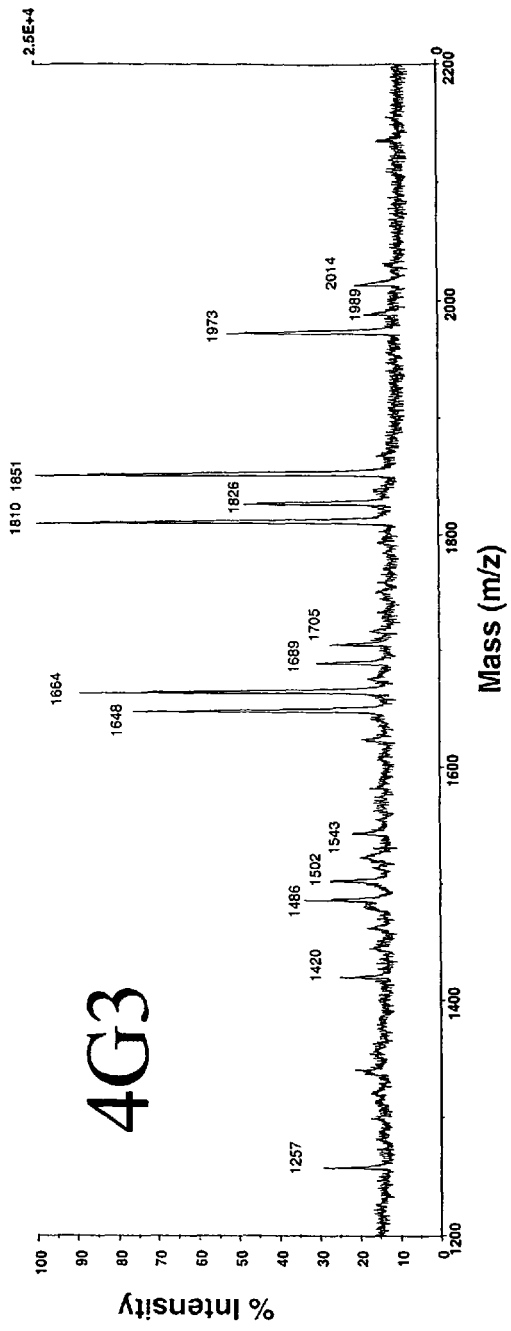
Figure 8D:
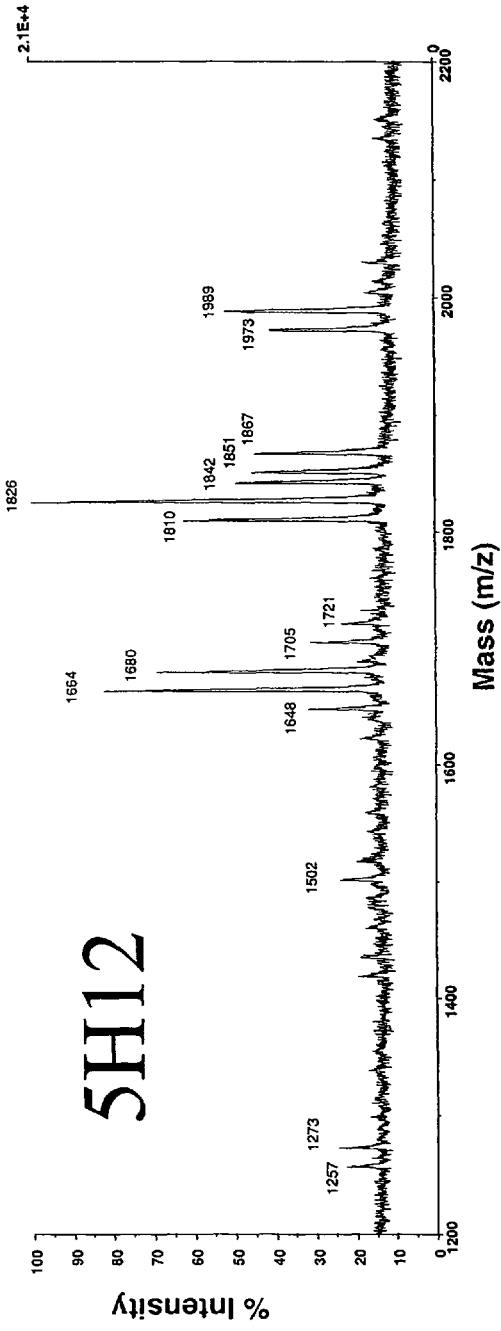

Oligosaccharides derived from the mAb sample produced in wt-chG250-SP2/0 cell line, that does not express GnTIII, contained nonbisected biantennary complex (m/z 1486) and mono- or di-galactosylated nonbisected biantennary complex structures (FIG. 7A), both α(1,6)-fucosylated in the core region (peaks m/z 1648 and 1810 respectively).

Expression of GnTIII generated bisected $F_c$-associated oligosaccharide structures of two types: complex or hybrid. Complex bisected oligosaccharides were unequivocally assigned to peaks at m/z 1543, 1689, 1705, 1851 and 1867 ([M+K$^+$] adduct). As expected, the increase in bisected oligosaccharides was accompanied by a concomitant reduction of peaks m/z 1486 and 1648, that correspond to nonbisected complex oligosaccharides. For all samples derived from the GnTIII expressing clones, the main substrate of GnTIII (m/z 1486) decreased dramatically. As expected, the percentage of the nonbisected complex oligosaccharide type, assigned to peak at m/z 1648, had the lowest values for the clones expressing the highest GnTIII levels (clones 4E6, 4E8, 5G2 and 5H12). These two peaks decreased in favor of the accumulation of bisected complex and bisected hybrid type oligosaccharides (FIGS. 7A-7D and 8A-8D). The percentage of bisected complex oligosaccharides was higher for the samples derived from the clones expressing lower amounts of GnTIII. This is consistent with the fact that a higher GnTIII expression level probably shifts the biosynthetic flux to bisected hybrid structures, thereby decreasing the relative proportions of complex and complex bisected compound. For bisected hybrid structures, two possible structures could sometimes be assigned to a single peak. Therefore, some assumptions were made in order to approximate the percentage of these structures over the total oligosaccharide pool. Peaks m/z 1664, 1680, 1810 and 1826 can be assigned to either bisected hybrid type, to galactosylated complex oligosaccharides, or a mixture of them. Due to the fact that the wt-antibody preparation had a relatively low percentage of peak 1664, it was assumed that this peak, appearing in significant amounts in the antibody samples derived from the different clones, corresponded entirely to bisected hybrid structures (FIGS. 7A-7D and 8A-8D). However to assign a specific structure to peaks m/z 1810 and 1826 further characterization has to be performed. In summary, by overexpression of GnTIII, bisected oligosaccharides structures were generated and their relative proportions correlated with GnTIII expression levels.

6. Measurement of Antibody Mediated Cytotoxic Activity by Calcein-AM Retention

The Calcein-AM retention method of measuring cytotoxicity measures the dye fluorescence remaining in the cells after incubation with the antibody. Four million G250 antigen-positive cells (target) were labelled with 10 μM Calcein-AM (Molecular Probes, Eugene, Oreg.) in 1.8 mL RPMI-1640 cell culture medium (GIBCO BRL, Basel, Switzerland) supplemented with 10% fetal calf serum for 30 min at 37° C. in a 5% $CO_2$ humidified atmosphere. The cells were washed twice in culture medium and resuspended in 12 mL AIMV serum free medium (GIBCO BRL, Basel, Switzerland). Labelled cells were then transferred to U-bottom 96-wells (30,000 cells/well) and incubated in triplicate with different concentrations of antibody for 1 hour at 4° C. Peripheral blood mononuclear cells (PBMC) were separated from heparinated fresh human blood (in all experiments obtained from the same healthy donor) by centrifugation over a Ficoll-Paque (Pharmacia Biotech, Dübendorf, Switzerland) gradient. PBMCs were added in triplicate wells in a 50 μL volume, yielding an effector to target ratio (E:T ratio) of 25:1 and a final volume of 200 μL. The 96-well plate was then incubated for 4 hours at 37° C. in a 5% $CO_2$ atmosphere. Thereafter the 96-well plate was centrifuged at 700×g for 5 min and the supernatants were discarded. The cell pellets were washed twice with Hank's balanced salt solution (HBSS) and lysed in 200 μL 0.05M sodium borate, pH 9, 0.1% Triton X-100. Retention of the fluorescent dye in the target cells was measured with a FLUOstar microplate reader (BMG LabTechnologies, Offenburg, Germany). The specific lysis was calculated relative to a total lysis control, resulting from exposure of the target cells to saponin (200 mg/mL in AIMV; SIGMA, Buchs, Switzerland) instead of exposure to antibody. Specific lysis (%) was calculated with the following formula:

$$\% \text{ Cytotoxicity} = \frac{F_{med} - F_{exp}}{F_{med} - F_{det}}$$

where $F_{med}$ represents the fluorescence of target cells treated with medium alone and considers unspecific lysis by PMBCs, $F_{exp}$ represents the fluorescence of cells treated with antibody and $F_{det}$ represents the fluorescence of cells treated with saponin instead of antibody.

To determine the effect of modified glycosylation variants of chG250 on the in vitro ADCC activity, G250 antigen-positive target cells were cultured with PBMCs with and without chG250 antibody samples at different concentrations. The cytotoxicity of unmodified chG250 antibody derived from the wild type cell line was compared with two antibody preparations derived from two cell lines (3D3, 5H12) expressing intermediate and high GnTIII levels, respectively (see FIG. 5).

Figure 9:
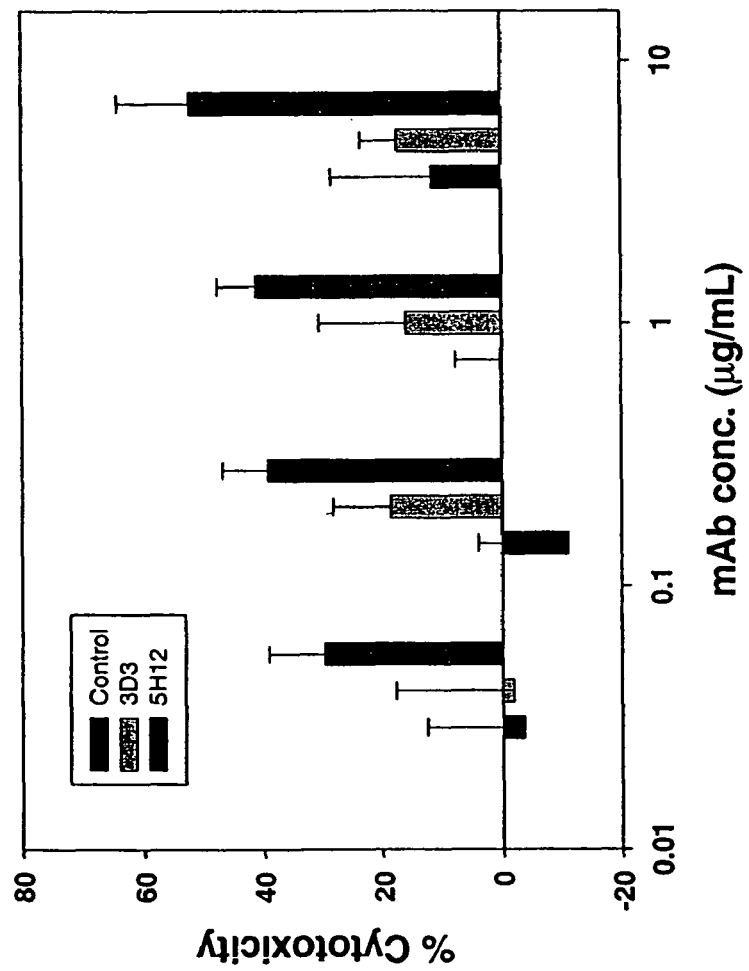
FIG. 9. In vitro ADCC assay of antibody samples derived from control wt-chG250-SP2/-cells and GnTIII transected clones 3D3 and 5H12.

Unmodified chG250 antibody did not mediate significant ADCC activity over the entire concentration range used in the assay (the activity was not significantly different from background). Augmented ADCC activity (close to 20%, see FIG. 9) at 2 μg/mL was observed with the antibody sample derived from clone 3D3, which expressed intermediate GnTIII levels. The cytotoxic activity of this antibody samples did not grow at higher antibody concentrations. As expected the antibody preparation derived from clone 5H12 showed a striking increase over samples 3D3 and unmodified antibody in its ability to mediate ADCC against target cells. The maximal ADCC activity of this antibody preparation was around 50% and was remarkable in mediating significant ADCC activity at 125-fold less concentrated when comparing with the unmodified control sample.

EXAMPLE 3

Treatment of Immune-Mediated Thrombocytopenia in a Patient with Chronic Graft-Versus-Host Disease Autoimmune thrombocytopenia in chronic graft-versus-host disease represents an instance of B-cell dysregulation leading to clinical disease. To treat immune-mediated thrombocytopenia in a subject with chronic graft-versus-host disease, an anti-CD20 chimeric monoclonal antibody prepared by the methods of the present invention and having increased ADCC is administered to the subject as described in Ratanatharathorn, V. et al., *Ann. Intern. Med.* 133(4):275-79 (2000) (the entire contents of which is hereby incorporated by reference). Specifically, a weekly infusion of the antibody, 375 mg/m² is administered to the subject for 4 weeks. The antibody therapy produces a marked depletion of B cells in the peripheral blood and decreased levels of platelet-associated antibody.

EXAMPLE 4

Treatment of Severe, Immune-Mediated, Pure Red Cell Aplasia and Hemolytic Anemia Immune-mediated, acquired pure red cell aplasia (PRCA) is a rare disorder frequently associated with other autoimmune phenomena To treat immune-mediated, acquired pure red cell aplasia in a subject, an anti-CD20 chimeric monoclonal antibody prepared by the methods of the present invention and having increased ADCC is administered to the subject as described in Zecca, M. et al., *Blood* 12:3995-97 (1997) (the entire contents of which are hereby incorporated by reference). Specifically, a subject with PRCA and autoimmune hemolytic anemia is given two doses of antibody, 375 mg/m², per week. After antibody therapy, substitutive treatment with intravenous immunoglobulin is initiated. This treatment produces a marked depletion of B cells and a significant rise in reticulocyte count accompanied by increased hemoglobin levels.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method of treating cancer in a mammal in need thereof comprising administering to said mammal a therapeutically effective amount of a composition comprising a glycoengineered, recombinant antigen binding molecule comprising an immunoglobulin Fc region containing N-linked oligosaccharides, produced by a eukaryotic cell line that expresses GnT III, wherein said glycoengineered, recombinant antigen binding molecule has increased bisecting GlcNAc residues on said N-linked oligosaccharides and increased Fc-mediated cellular cytotoxicity compared to a corresponding antibody that has not been glycoengineered, and wherein said eukaryotic cell is the CHO cell mutant lec 10.

2. A method of treating cancer in a mammal in need thereof comprising administering to said mammal a therapeutically effective amount of a composition comprising a glycoengineered, recombinant antigen binding molecule comprising an immunoglobulin Fc region containing N-linked oligosaccharides, produced by a eukaryotic cell line that expresses GnT III, wherein said glycoengineered, recombinant antigen binding molecule has increased bisecting GlcNAc residues on said N-linked oligosaccharides and increased Fc-mediated cellular cytotoxicity compared to a corresponding antibody that has not been glycoengineered, and wherein said eukaryotic cell is a CHO cell.

3. The method of claim 1 or 2, wherein said GnT III is expressed in an amount sufficient to increase the proportion of said polypeptides carrying bisected hybrid oligosaccharides or galactosylated complex oligosaccharides or mixtures thereof in the Fc region relative to polypeptides carrying bisected complex oligosaccharides in the Fc region.

4. The method of claim 1 or 2, wherein a nucleic acid molecule comprising at least one gene encoding GnT III has been introduced into said eukaryotic cell.

5. The method of claim 2, wherein said eukaryotic cell has been engineered such that an endogenous GnT III gene is activated.

6. The method of claim 5, wherein said endogenous GnT III has been activated by insertion of a DNA element which increases gene expression into the host chromosome.

7. The method of claim 4, wherein said at least one gene encoding GnT HI has been introduced into said host cell chromosome.

8. The method of claim 5, wherein said endogenous GnT III has been activated by insertion of a promoter element, a transposon, or a retroviral element into the host cell chromosome.

9. The method of claim 4, wherein said at least one nucleic acid encoding a GnT III is operably linked to a constitutive promoter element.

10. The method of claim 1 or 2, wherein said recombinant antigen binding molecule is selected from the group consisting of: an antibody, an antibody fragment and a fusion protein that includes a region equivalent to the Fc region of an immunoglobulin.

11. The method of claim 10, wherein said recombinant antigen binding molecule is a fusion protein that includes a region equivalent to the Fc region of a human immunoglobulin.

12. The method of claim 10, wherein said recombinant antigen binding molecule is an antibody.

13. The method of claim 12, wherein said antibody is selected from the group consisting of: an anti-CD20 antibody, the chimeric anti-human neuroblastoma monoclonal antibody chCE7, the chimeric anti-human renal cell carcinoma monoclonal antibody chG250, the chimeric anti-human colon, lung, and breast carcinoma monoclonal antibody ING-1, the humanized anti-human 17-1A antigen monoclonal antibody 3622W94, the humanized anti-human colorectal tumor antibody A33, the anti-human melanoma antibody directed against GD3 ganglioside R24, the chimeric anti-human squamous-cell carcinoma monoclonal antibody SF-25, an anti-human EGFR antibody, an anti-human EGFRvIII antibody, an anti-human PSMA antibody, an anti-human PSCA antibody, an anti-human CD22 antibody, an anti-human CD30 antibody, an anti-human CD33 antibody, an anti-human CD38 antibody, an anti-human CD40 antibody, an anti-human CD45 antibody, an anti-human CD52 antibody, an anti-human CD138 antibody, an anti-human HLA-DR variant antibody, an anti-human EpCAM antibody, an anti-human CEA antibody, an anti-human MUC1 antibody, an anti-human MUC1 core protein antibody, an anti-human aberrantly glycosylated MUC1 antibody, an antibody against human fibronectin variants containing the ED-B domain, and an anti-human HER2/neu antibody.

14. The method of claim 1 or 2, wherein said cancer is selected from the group consisting of: neuroblastoma, renal cell carcinoma, colon carcinoma, lung carcinoma, melanoma, human squamous-cell carcinoma, human small cell lung carcinoma, rectal carcinoma, ovarian carcinoma, acute myelogneous leukemia, malignant glioma, colorectal carcinoma, kidney carcinoma, prostate carcinoma, pancreas carcinoma, CD20 B-cell lymphoma, CD20-positive low-grade lymphoma, follicular Non-Hodgkin's lymphoma and breast cancer.

15. The method of claim 1 or 2, wherein said mammal is a human.

16. The method of claim 1 or 2, wherein said composition further comprises a pharmaceutically acceptable carrier.

17. The method of claim 16, wherein said composition further comprises a cytokine.

18. The method of claim 1 or 2, wherein the method of administration is selected from the group consisting of: intravenous infusion, parenteral injection and subcutaneous injection.

19. The method of claim 1 or 2, wherein said increased Fc-mediated cellular cytotoxicity is increased ADCC.

UNITED STATES PATENT AND TRADEMARK OFFICE
CERTIFICATE OF CORRECTION

PATENT NO. : 8,021,856 B2  
APPLICATION NO. : 11/199232  
DATED : September 20, 2011  
INVENTOR(S) : Pablo Umaña et al.

Page 1 of 1

It is certified that error appears in the above-identified patent and that said Letters Patent is hereby corrected as shown below:

In the Claims:

Column 27, Line 56, in claim 7, "GnT HI" should be replaced with "GnT III".

Signed and Sealed this
Twenty-eighth Day of January, 2014

Michelle K. Lee
*Deputy Director of the United States Patent and Trademark Office*